US008240468B2

(12) United States Patent
Wilkinson et al.

(10) Patent No.: US 8,240,468 B2
(45) Date of Patent: Aug. 14, 2012

(54) PREPACKAGED MEDICAL DEVICE AND PACKAGING TRAY

(75) Inventors: Bradley Wilkinson, North Haledon, NJ (US); Jamieson Crawford, Cliffside Park, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 867 days.

(21) Appl. No.: 11/408,788

(22) Filed: Apr. 21, 2006

(65) Prior Publication Data
US 2006/0282045 A1    Dec. 14, 2006

Related U.S. Application Data

(60) Provisional application No. 60/674,064, filed on Apr. 22, 2005.

(51) Int. Cl.
*B65D 83/10* (2006.01)
(52) U.S. Cl. ................ 206/364; 206/363; 206/438
(58) Field of Classification Search ............. 206/363, 206/571, 370, 562, 570, 527, 364, 365, 366, 206/367, 368, 369, 438, 439, 440, 572, 563, 206/564; 220/527, 528
See application file for complete search history.

(56) References Cited

U.S. PATENT DOCUMENTS

| | | | |
|---|---|---|---|
| 2,720,969 A | 10/1955 | Kendall | |
| 3,013,656 A | 12/1961 | Murphy | |
| 3,035,691 A | 5/1962 | Rasmussen et al. | |
| 3,485,352 A | 12/1969 | Pilger | |
| 3,696,920 A | 10/1972 | Lahay | |
| 3,750,875 A | 8/1973 | Juster | |
| 3,952,873 A | 4/1976 | Pampuch et al. | |
| 4,019,633 A | 4/1977 | Roth | |
| 4,184,593 A | 1/1980 | Dorr | |
| 4,216,860 A | 8/1980 | Heimann | |
| 4,332,322 A | 6/1982 | Jaeschke et al. | |
| 4,438,845 A | 3/1984 | Mochow | |
| 4,592,744 A | 6/1986 | Jagger et al. | |
| 4,657,138 A * | 4/1987 | Watson | 206/366 |
| 4,731,059 A | 3/1988 | Wanderer et al. | |
| 4,747,831 A | 5/1988 | Kulli | |
| 4,846,808 A | 7/1989 | Haber et al. | |
| 4,850,374 A | 7/1989 | Diaz-Ramos | |

(Continued)

FOREIGN PATENT DOCUMENTS

EP    1293222 A    3/2003

(Continued)

*Primary Examiner* — J. Gregory Pickett
*Assistant Examiner* — Ernesto Grano
(74) *Attorney, Agent, or Firm* — The Webb Law Firm

(57) ABSTRACT

A pre-packaged medical device includes a tray supporting a medical device such as a blood collection set including a needle assembly and a tube holder. The tray defines a first contoured portion supporting at least a portion of the needle assembly and a second contoured portion supporting the tube holder. The tray may have a tray body with a plurality of posts upstanding from a bottom wall in the first contoured portion for engaging the needle assembly. The posts may be positioned to maintain the needle assembly in a defined orientation while preventing the inadvertent actuation of the needle assembly, which may include a spring-driven safety shield. The configuration of the pre-packaged medical device allows sequential removal of the blood collection set, typically in the order of intended use including first removal of a needle assembly, second removal of tubing, and third removal of the tube holder.

22 Claims, 25 Drawing Sheets

U.S. PATENT DOCUMENTS

| | | | |
|---|---|---|---|
| 4,871,355 A | 10/1989 | Kikkawa | |
| 4,900,307 A | 2/1990 | Kulli | |
| 4,942,881 A | 7/1990 | Al-Sioufi et al. | |
| 4,988,339 A | 1/1991 | Vadher | |
| 4,991,601 A | 2/1991 | Kazai et al. | |
| 4,993,426 A | 2/1991 | Spencer | |
| 4,994,034 A | 2/1991 | Botich et al. | |
| 5,030,209 A | 7/1991 | Wanderer et al. | |
| 5,031,775 A | 7/1991 | Kane | |
| 5,062,837 A | 11/1991 | Al-Sioufi et al. | |
| 5,067,490 A | 11/1991 | Haber | |
| 5,069,225 A | 12/1991 | Okamura | |
| RE33,952 E | 6/1992 | Bonaldo | |
| 5,120,311 A | 6/1992 | Sagstetter et al. | |
| 5,178,282 A * | 1/1993 | Williams | 206/570 |
| 5,188,599 A | 2/1993 | Botich et al. | |
| 5,217,025 A | 6/1993 | Okamura | |
| 5,219,333 A | 6/1993 | Sagstetter et al. | |
| 5,284,244 A * | 2/1994 | O'Toole et al. | 206/363 |
| 5,300,039 A | 4/1994 | Poulsen | |
| 5,318,543 A * | 6/1994 | Ross et al. | 604/170.01 |
| 5,392,918 A | 2/1995 | Harrison | |
| 5,407,070 A | 4/1995 | Bascos et al. | |
| 5,407,431 A | 4/1995 | Botich et al. | |
| 5,413,083 A | 5/1995 | Jones | |
| 5,485,917 A * | 1/1996 | Early | 206/363 |
| 5,501,675 A | 3/1996 | Erskine | |
| 5,527,294 A | 6/1996 | Weatherford et al. | |
| 5,540,651 A | 7/1996 | Risch et al. | |
| 5,613,500 A | 3/1997 | Bishop | |
| 5,616,135 A | 4/1997 | Thorne et al. | |
| 5,616,136 A | 4/1997 | Shillington et al. | |
| 5,637,101 A | 6/1997 | Shillington | |
| 5,685,863 A | 11/1997 | Botich et al. | |
| 5,690,222 A | 11/1997 | Peters | |
| 5,693,028 A | 12/1997 | Shillington | |
| 5,755,673 A | 5/1998 | Kinsey | |
| 5,769,826 A | 6/1998 | Johnson et al. | |
| 5,797,490 A | 8/1998 | Fujii et al. | |
| 5,800,395 A | 9/1998 | Botich et al. | |
| 5,800,404 A | 9/1998 | Poulsen | |
| 5,810,775 A | 9/1998 | Shaw | |
| 5,947,284 A | 9/1999 | Foster | |
| 6,004,278 A | 12/1999 | Botich et al. | |
| 6,024,727 A | 2/2000 | Thorne et al. | |
| 6,047,826 A | 4/2000 | Kalinski et al. | |
| 6,063,040 A | 5/2000 | Owen et al. | |
| 6,068,121 A * | 5/2000 | McGlinch | 206/364 |
| 6,074,373 A | 6/2000 | Sudo et al. | |
| 6,077,244 A | 6/2000 | Botich et al. | |
| 6,090,078 A | 7/2000 | Erskine | |
| 6,096,005 A | 8/2000 | Botich et al. | |
| 6,127,320 A | 10/2000 | van Ooij et al. | |
| 6,146,337 A | 11/2000 | Polidoro et al. | |
| 6,210,371 B1 | 4/2001 | Shaw | |
| D462,901 S | 9/2002 | Giard, Jr. et al. | |
| 6,622,864 B1 * | 9/2003 | Debbs et al. | 206/438 |
| D480,816 S * | 10/2003 | McMichael et al. | D24/229 |
| 2003/0062281 A1 | 4/2003 | Giard, Jr. et al. | |
| 2003/0159967 A1 | 8/2003 | McMichael et al. | |
| 2003/0199830 A1 | 10/2003 | Nguyen | |
| 2004/0195132 A1* | 10/2004 | Sheetz et al. | 206/438 |
| 2004/0243214 A1* | 12/2004 | Farrell et al. | 623/1.11 |

FOREIGN PATENT DOCUMENTS

| | | |
|---|---|---|
| JP | 2003230550 A | 8/2003 |
| WO | 9923947 | 5/1999 |
| WO | 0012160 | 3/2000 |
| WO | 0047256 | 8/2000 |
| WO | 0105855 | 2/2003 |

* cited by examiner

PREPACKAGED MEDICAL DEVICE AND PACKAGING TRAY

The present application claims priority to provisional application No. 60/674,064 filed on Apr. 22, 2005.

BACKGROUND OF THE INVENTION

1. Field of the Invention

The subject invention relates to a pre-packaged medical device including a tray supporting a medical device, such as a blood collection set with an attached tube holder, and to the assembly and positioning of the blood collection set and attached tube holder within the tray. The invention also relates to a method for packaging a medical device such as a blood collection set having an attached tube holder within the tray.

2. Description of Related Art

A blood collection set is used to access a blood vessel of a patient and to draw blood from the patient. The blood collection set typically includes a needle cannula with a proximal end, a sharply pointed distal end, and a lumen extending between the ends. The proximal end of the needle cannula is typically mounted to a plastic hub. The hub is formed with an axial passage that communicates with the lumen through the needle cannula. Flexible tubing of appropriate length is mounted to the end of the hub opposite the needle cannula, and a fitting is mounted to the end of the plastic tubing remote from the needle hub. The fitting may be configured for mating with a container, such as an evacuated blood collection tube or a blood bag, or a holder to secure such container. Thus, the blood collection set may be used to deliver a sample of blood from a patient to a container.

Many blood collection sets include a safety shield that is retained in a proximal position on the needle hub prior to use of the blood collection set. After use, however, the safety shield is moved distally relative to the needle hub to a position where the safety shield surrounds the needle cannula. Some such shielding operations may be carried out manually. Thus, the user may hold the proximal end of the hub and/or the plastic tubing in one hand and move the shield distally with the other hand. The shield often locks with structure on the hub to prevent the shield from sliding completely off the hub and to prevent re-exposure of the needle cannula.

More recent developments in blood collection sets include automatically actuated safety shielding. For example, a spring may be disposed between the needle hub and the safety shield. A latch retains the safety shield in the proximal position on the hub and against the force of the spring. However, a push button actuator releases the latch in response to digital pressure by the user. The spring then propels the shield distally and into a shielding disposition around the needle cannula.

Many medical devices, including blood collection sets, are packaged in sterile blister packages. The typical prior art blister package includes a standard plastic tray for storing the medical device and a plastic cover removably secured across peripheral regions of the standard plastic tray.

Few blister packages provide sufficient compressive structural rigidity and/or protection of the actuator button. Thus, there remains the possibility that the medical device may shift and the actuator button of the blood collection set will be triggered inadvertently by forces exerted on the blister package during storage or shipment, or by forces generated when a user manually grips a blister package. In addition, known blister packages have not been designed to accommodate or nest with other blister packages within the same case to further prevent inadvertent activation of the blood collection set actuator button.

An inadvertent depression of the actuator button could urge the automatic safety shield distally relative to the needle cannula and will lock the shield in a position that prevents further use of the needle cannula. Thus, an unused blood collection set may have to be discarded due to an inadvertent actuation of the safety shielding caused by ordinary gripping of the blister package in which the blood collection set is sealed.

The fitting at the end of the plastic tube opposite the needle hub may include a second needle cannula for extending through the seal of an evacuated blood collection tube during use. Forces on the blister package could deform the blister package sufficiently for the needle to be urged through either the walls of the tray or through the plastic cover of the blister package. A protruding needle cannula would create the risk for an accidental needle stick. Additionally, prior art blood collection sets typically further require a band to maintain the tubing in an orderly coil within the confines of the blister package. Such a band accomplishes the task of controlling the tubing, but adds to the cost and time to complete the packaging of the blood collection set.

Accordingly, a need exists for an improved package and method for storing and transporting medical devices that provides easy and simple assembly of the medical device in the package, adequately restrains and protects the medical device during transport, is easily transported, and is easy for the end user to open to access and remove the device.

SUMMARY OF THE INVENTION

The prepackaged medical device typically supports a blood collection set comprising a needle assembly, tube holder and length of tubing connecting the needle assembly and tube holder. A method for packaging the blood collection set is also set forth in this disclosure.

The prepackaged medical device, in one embodiment, houses a medical device comprising a blood collection set comprising a needle assembly with a needle cannula. The needle cannula typically has a proximal end, a sharply pointed distal end, and a lumen extending between the ends. The needle assembly further typically includes a plastic hub with a proximal end, a distal end, and a passage extending between the ends. The proximal end of the needle cannula is securely mounted in the distal end of the hub.

The needle assembly may further include a safety cap with a rigid tubular sidewall and an open proximal end. The open proximal end of the safety cap may telescope in a distal-to-proximal direction over the needle cannula and may optionally be retained frictionally in proximity to the needle hub. The safety cap may be adapted to separate from the hub to expose the needle cannula immediately prior to use. The needle assembly may also include a safety shield that is adapted to be telescoped over the needle hub after use. The safety shield may be characterized by opposite, outward-directed flexible wings. The safety shield may be moved from a proximal position where the needle cannula is exposed to a distal position where the needle cannula is protectively enclosed within the safety shield. Locking structures may be provided on the hub and the safety shield to prevent movement of the safety shield distally beyond the needle cannula. Additionally, locking structures are provided to prevent re-exposure of a properly shielded needle cannula.

The safety shield may include an actuating window. A resiliently deflectable actuating button may project from the needle hub and pass into the actuating window when the safety shield is in its proximal position. Release of the resiliently deflectable actuating button from the actuating window permits the needle cannula to move to the proximal position.

The needle assembly may further comprise a spring disposed between a portion of the needle hub and the safety shield. The spring is disposed to retain stored energy when the needle cannula is in its distal position. However, disengagement of the actuating button from the actuating window releases the stored energy in the spring and enables the spring to propel the needle cannula into its proximal position surrounding the needle cannula.

The flexible tubing associating the needle assembly and tube holder has a proximal end and a distal end. The distal end of the flexible tubing is securely connected to the proximal end of the needle hub. The length of tubing may vary depending upon the application for which it will be used. Such variation requires careful attention to the design of the packaging for the medical device so it may prove effective in accommodating varying lengths of tubing and proper positioning of the needle assembly and tube holder in the packaging.

The blood collection set may include a fitting securely mounted to the distal end of the flexible tubing. The fitting may be configured to engage another fitting or to receive a second needle cannula. Alternatively, the fitting may have a second needle cannula permanently mounted thereon and engageable with an evacuated blood collection tube. However, the fitting may also take the form of the tube holder attached at its distal end to the tubing.

In general, the prepackaged medical device comprises the blood collection set described hereinabove and a tray supporting the medical device. The tray generally comprises a tray body, typically a unitary tray body, defining a first contoured portion supporting and maintaining positioning of the needle assembly, and a second contoured portion supporting and maintaining positioning of the tube holder. The first and second contoured portions are typically formed in spaced relation to allow sequential removal of the needle assembly, tubing, and tube holder, typically first removal of the needle assembly, second removal of the tubing, and third removal of the tube holder. A removable lid may enclose the medical device. The tray body may be molded unitarily from a plastic material such as polyvinylchloride (PVC), polyethylene terephthalate (PET), or polyethylene terephthalate glycol (PETG), also known as glycolised polyester, in which the "G" represents glycol modifiers which are incorporated to minimize brittleness and premature aging that occur in unmodified amorphous polyethylene terephthalate (PET).

The tray body typically defines a peripheral flange upon which the lid is engaged. The flange may include at least one lip for maintaining the position of the tubing within the tray body until the needle assembly is removed.

At least a portion of the second contoured portion may depend from a bottom wall of the tray body and is formed to accept the tube holder.

The needle assembly may comprise a pair of outward-extending wings and the tray body may comprise a bottom wall and a plurality of posts upstanding from the bottom wall in the first contoured portion, with the posts positioned to maintain a defined orientation of the wings until removal of the needle assembly. The plurality of posts may be arranged to allow the wings to be oriented in two generally oppositely facing orientations. One of the orientations may be for tubing of length X and the other orientation may be for tubing having a length longer or shorter than length X by at least about 20 percent based on the length of the tubing, such as by about two inches.

The tray body may comprise a bottom wall and at least one post upstanding from the bottom wall and adapted to maintain the positioning of the tubing relative to the needle assembly. The needle assembly may comprise a distally-extending needle cannula, and the at least one post may be positioned to maintain the positioning of the tubing relative to the needle cannula to prevent damage to the tubing during shipment of the prepackaged medical assembly. The relative positioning between the tubing and the needle cannula may comprise the needle cannula restraining the tubing against the bottom wall of the tray body.

Additionally, the needle assembly may comprise a distally-extending needle cannula and a shield enclosing the needle cannula, and the at least one post may be positioned to maintain the positioning of the tubing relative to the shield to prevent the tubing from interfering with the shield during removal of the needle assembly. The relative positioning between the tubing and shield may comprise the shield restraining the tubing against the bottom wall of the tray body.

The tray body may further comprise a third contoured portion depending from the bottom wall at a position opposite from the second contoured portion, with the second and third contoured portions formed to allow the tray body to nest with other tray bodies.

Another embodiment of the invention provides a medical kit comprising a needle assembly, a fitting, a tube holder, and a length of tubing connecting the needle assembly and the fitting, and a tray supporting the components of the kit. The tray generally comprises a tray body, typically a unitary tray body, defining a first contoured portion supporting and maintaining positioning of the needle assembly, and a second contoured portion supporting and maintaining positioning of the tube holder. The first and second contoured portions are typically formed in spaced relation to allow first removal of the needle assembly, second removal of the tubing, and third removal of the tube holder. A removable lid may enclose the tray body.

Another embodiment of the invention provides a tray for supporting a medical device. The tray generally comprises a unitarily formed tray body defining a first contoured portion adapted to support and maintain positioning of a needle assembly of the medical device and a second contoured portion adapted to support and maintain positioning of a tube holder associated with the needle assembly. The first and second contoured portions may be formed in spaced relation to allow independent removal of the needle assembly and the tube holder.

The tray body may comprise a bottom wall and a plurality of posts upstanding from the bottom wall in the first contoured portion to engage and restrain the needle assembly.

The tray body may comprise a peripheral flange for accepting a lid to enclose the tray body, and the flange may comprise at least one lip for maintaining the positioning of tubing within the tray body associated with the needle assembly and the tube holder.

The posts may be arranged to allow the needle assembly to be oriented in two generally oppositely facing orientations.

At least one post upstanding from the bottom wall may be spaced from the posts in the first contoured portion and be adapted to maintain the positioning of tubing associated with the needle assembly and the tube holder.

At least a portion of the second contoured portion may depend from a bottom wall of the tray body, and the tray body may further comprise a third contoured portion depending from the bottom wall at a position opposite form the second contoured portion, such that the second and third contoured portions allow the tray body to nest with other tray bodies or stand stable on a flat surface.

As indicated, an embodiment of the invention is a method of packaging a medical device. The method generally comprises providing a medical device, providing a tray for supporting the medical device, and placing the medical device in the tray. The medical device may comprise a needle assembly, a tube holder, and a length of tubing extending between the needle assembly and the tube holder. The tray may comprise a tray body, typically a unitary tray body, defining a first contoured portion for supporting and maintaining positioning of the needle assembly and a second contoured portion for supporting and maintaining positioning of the tube holder. The medical device may be placed in the tray such that the needle assembly is inserted in the first contoured portion and the tube holder in inserted in the second contoured portion. The first and second contoured portions may be formed in spaced relation to allow first removal of the needle assembly, second removal of the tubing, and third removal of the tube holder.

The tray body may define a peripheral flange, and the method may comprise sealing a lid against the flange to enclose the medical device. The flange may comprise at least one lip, and the method may further comprise maintaining the positioning of the tubing within the tray body with the lip.

The tray body may comprise a bottom wall and at least one post upstanding from the bottom wall, and the method may further comprise maintaining the positioning of the tubing relative to the needle assembly with the post. The needle assembly may comprise a distally-extending needle cannula, and the method may further comprise the needle cannula restraining the tubing against the bottom wall of the tray body. Additionally, the needle cannula may be shielded by a shield enclosing the needle cannula, and the method may further comprise the shield restraining the tubing against the bottom wall of the tray body.

Further, tray body may comprise a bottom wall and a plurality of posts upstanding from the bottom wall in the first contoured portion, such that the needle assembly is inserted into engagement with the posts in the first contoured portion.

The tray body also has the added benefit of orientating the needle assembly in the blister package between the posts in such a way as to facilitate removal and prevent activation during removal. The location of the posts relative to the push button and shield are such that the user is guided to remove the needle assembly by grabbing either the wings or the needle hub. This prevents the button from being activated during removal and orients the needle assembly in the hand for immediate use.

In a further embodiment, the invention provides a prepackaged medical device comprising a medical device including a needle assembly, a tube holder, and a length of tubing extending between the needle assembly and the tube holder, as well as a tray supporting the medical device. The tray includes a tray body defining a first contoured portion supporting and maintaining positioning of the needle assembly and a second contoured portion supporting and maintaining positioning of the tube holder. The first contoured portion comprises structure adapted to maintain the needle assembly within the tray body in at least two distinct orientations with respect to the orientation of the tube holder maintained within the tray body. Desirably, the structure of the first contoured portion maintains the needle assembly within the tray body in a first orientation for accommodating tubing having a length X and in a second orientation for accommodating tubing having a length longer or shorter than length X by at least about 20 percent.

In yet a further embodiment, the invention provides a prepackaged medical device comprising a medical device including a needle assembly, a tube holder, and a length of tubing extending between the needle assembly and the tube holder, as well as a tray supporting the medical device. The tray comprises a tray body defining a first contoured portion supporting and maintaining positioning of the needle assembly, a second contoured portion depending from a bottom wall of the tray body for supporting and maintaining positioning of the tube holder, and a third contoured portion depending from the bottom wall of the tray body at a position opposite from the second contoured portion. The second and third contoured portions are formed to allow the tray body to nest with other tray bodies.

Desirably, the second and third contoured portions extend from the bottom wall of the tray body such that a plane extending across bottom portions of the second and third contoured portions is generally parallel with the bottom wall of the tray body.

In one aspect, the second contoured portion comprises a protuberance and the third contoured portion comprises a valley formed between a pair of bumps, with the valley of the third contoured portion of one tray body being formed to accommodate the protuberance of the second contoured portion of another tray body when two tray bodies are nested. In this manner, when two trays are in a nested relationship, rotational movement of one tray body with respect to the other tray body is prevented, thereby facilitating packaging and handling.

Further details and advantages of the invention will become clear from the following detailed description when read in conjunction with the accompanying drawings.

DESCRIPTION OF THE PREFERRED EMBODIMENTS

Figure 1:
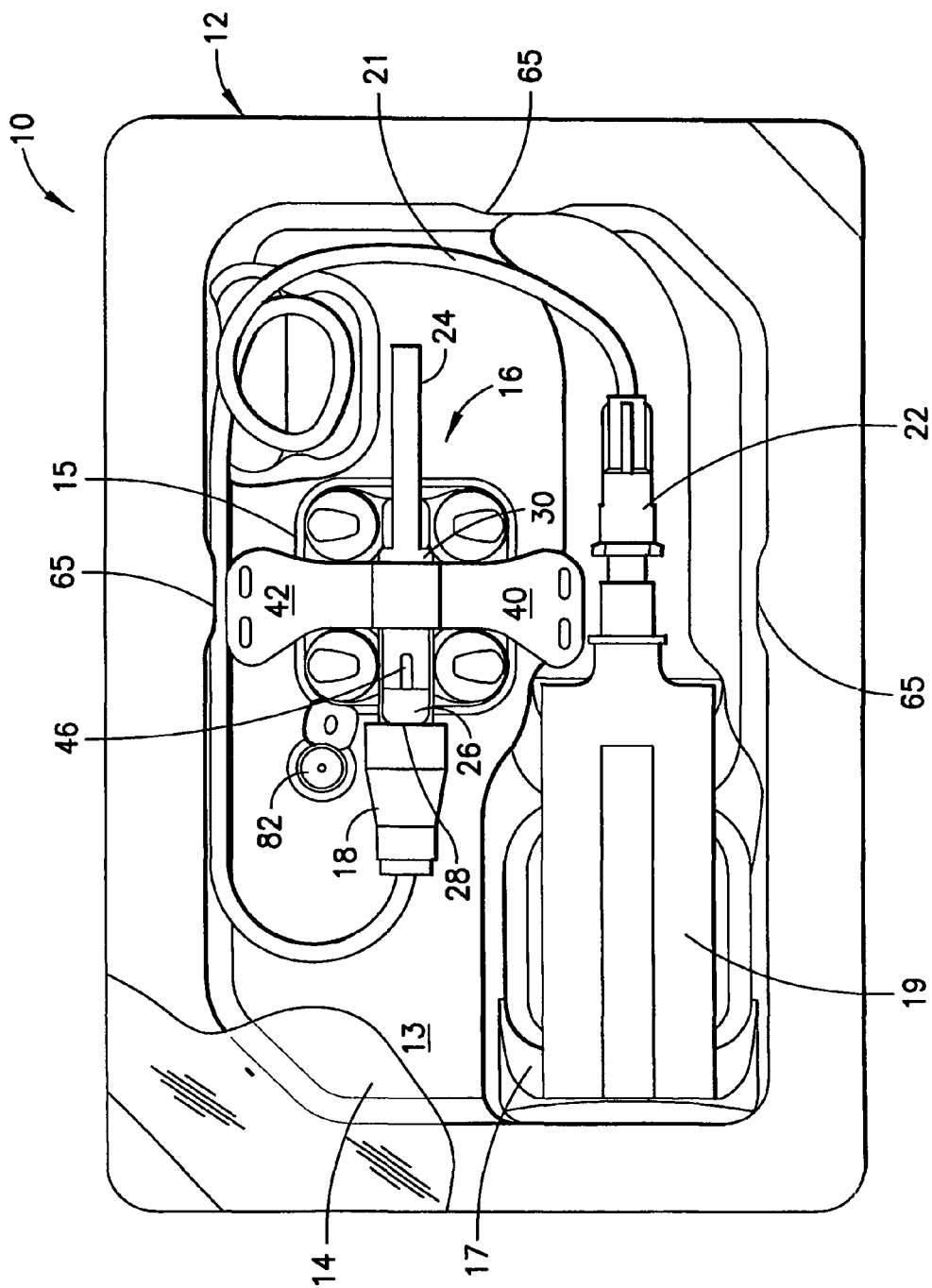
FIG. 1 is a top view of a prepackaged medical device having tubing of a first length.

For purposes of the description hereinafter, the words "upper", "lower", "right", "left", "vertical", "horizontal", "top", "bottom", "lateral", "longitudinal" and like spatial terms, if used, shall relate to the described embodiments as oriented in the drawing figures. However, it is to be understood that many alternative variations and embodiments may be assumed except where expressly specified to the contrary. It is also to be understood that the specific devices and embodiments illustrated in the accompanying drawings and described herein are simply exemplary embodiments of the invention.

Figure 2A:
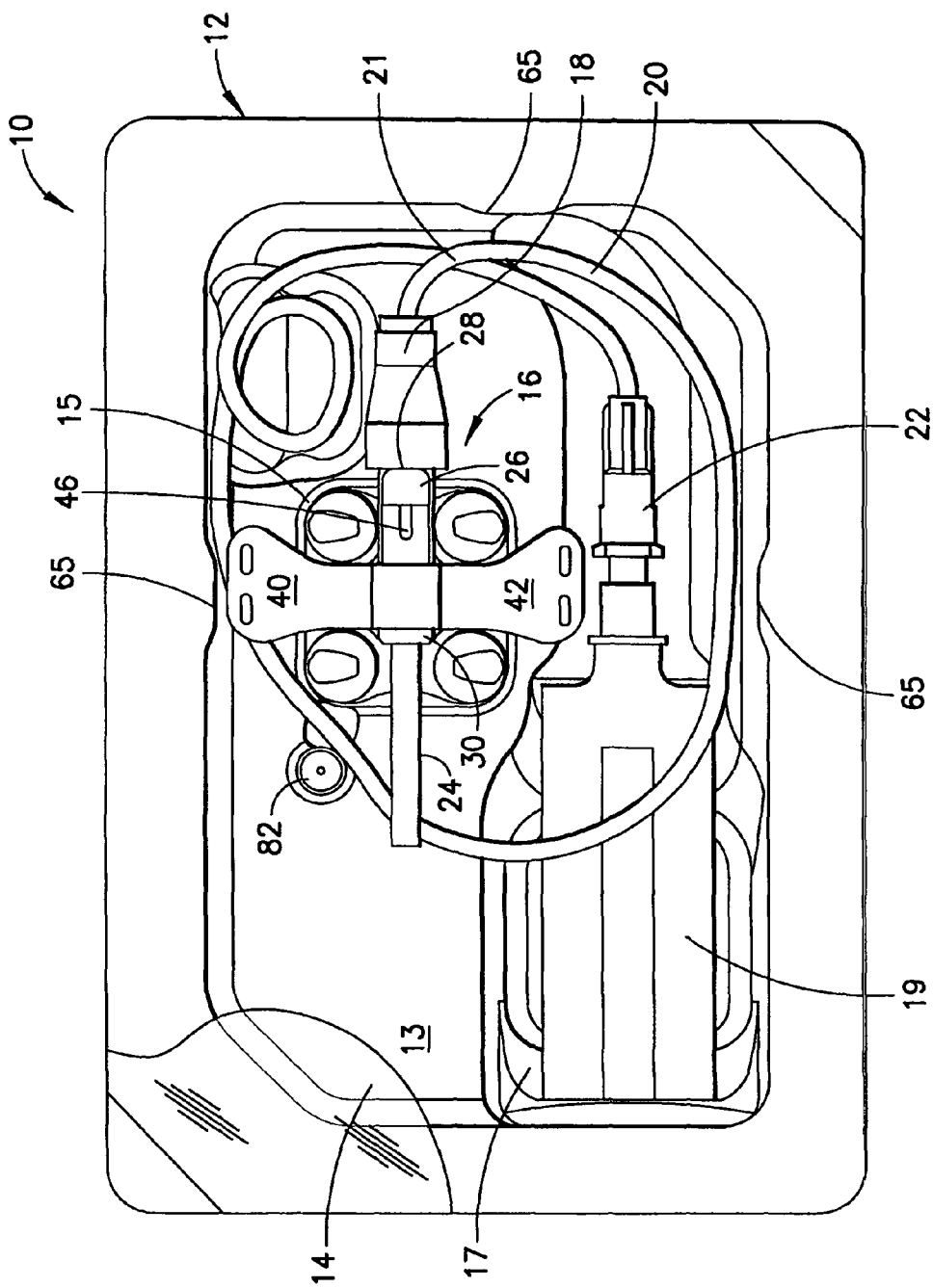
FIG. 2A is a top view of a prepackaged medical device having tubing of a second, longer length.

Referring to FIGS. 1 and 2A, a prepackaged medical device is identified generally by the numeral 10. Prepackaged medical device 10 generally includes a tray 12, a lid 14, and a blood collection set 16, typically including an attached tube holder 19 in one embodiment. Blood collection set 16 typically includes a needle assembly 18, a length of flexible tubing 20, 21 and a fitting 22 to which the tube holder 19 is associated in the illustrated embodiment. Needle assembly 18 includes a needle cannula and a needle hub, neither of which are illustrated in detail in the Figures, but are of conventional design. Needle assembly 18 may include a rigid tubular safety cap 24 telescoped over the needle cannula and removable from the body of the needle assembly 18 as is conventional in the art. The needle cannula (not shown) resides in safety cap 24 in a conventional manner. Safety cap 24 may be removed from needle assembly 18 by pulling safety cap 24 away from remaining portions of needle assembly 18 to expose the needle cannula as is known in the art.

Tray 12 supports and maintains the positioning of the blood collection set 16 and attached tube holder 19. As shown in detail in FIGS. 3-9, tray 12 comprises a tray body 13, typically a unitary tray body 13, which may define at least a first contoured portion 15 and a second contoured portion 17. As shown in FIGS. 1, 2A, and 10-15, the first contoured portion 15 generally supports and maintains the needle assembly 18 in a desired position as shown. The needle assembly 18 may be positioned in oppositely facing orientations as shown in FIGS. 1 and 2A. The second contoured portion 17 may additionally support and maintain the tube holder 19 and the fitting 22 as shown in the aforementioned drawings.

Needle assembly 18 may further include a safety shield 26. Safety shield 26 is a generally tubular structure with a rearward or proximal end 28, a forward or distal end 30, and a hollow space between ends 28 and 30 for accommodating the needle hub and/or portions of the needle cannula. The safety shield 26 is typically provided for protecting against inadvertent sticking after the needle assembly 18 has been actuated. Flexible wings 40 and 42 typically project transversely from safety shield 26 at locations near proximal end 30, usually adjacent the bottom of safety shield 26. Wings 40 and 42 may be folded into face-to-face engagement for facilitating digital manipulation of needle assembly 18. Alternatively, wings 40 and 42 may be laid flat and taped against the skin of a patient for maintaining the needle cannula in a desired position when in use.

Needle assembly 18 may comprise an actuating button 46 which may be located on a top surface of needle assembly 18, generally between wings 40 and 42 for actuating safety shield 26. Actuating button 46 typically extends from the needle hub and is engaged in an opening of the safety shield 26. Actuating button 46 retains safety shield 26 in the fixed position relative to the needle hub and the needle cannula prior to use, as illustrated in FIGS. 1 and 2A, for example. Actuating button 46 may be depressed relative to safety shield 26 to release safety shield 26 from the needle hub and the needle cannula after use of needle assembly 18 in a blood collection procedure. Needle assembly 18 typically further includes a coil spring (not shown) disposed in safety shield 26. The spring extends between the needle hub and the safety shield to effect relative movement with respect to each other upon actuation of the actuating button 46, such as to propel the needle hub rearward or proximally within the assembly 18 upon actuation of actuating button 46. The needle assembly 18 may also be configured with a safety shield 26 that is adapted to propel forward from the needle hub to encompass the needle cannula. Safety shield 26 may additionally have a reduced cross-section adjacent the opening where the actuating button 26 is positioned. The cross-sectional reduction may include concave arcuate reductions around all sides of safety shield 26 to facilitate the manipulation and actuation of needle assembly 18. Desirably, safety shield 26 has a maximum height that is less than the depth of the first contoured portion 15 of tray body 13. Actuating button 46 may also be recessed relative to portions of safety shield 26.

Flexible tubing 20, 21 extends from the needle assembly 18 for a selected length. Tray 12 is adapted to accommodate blood collection sets having different lengths of tubing. For example, FIG. 2A depicts blood collection set 16 having a first typical length of tubing, specifically about a twelve-inch length of tubing 20. An alternative flexible tubing 21 of a second length may also be employed, as shown in FIG. 1, which depicts blood collection set 16 with a seven-inch length of tubing 21. Desirably, tray 12 is adapted to accommodate various blood collection sets having different lengths of tubing, such as with one tubing defined by a first length X, and an alternate tubing defined by a second length which is longer or shorter than first length X by about 20 percent, such as by about two inches. Fitting 22 is mounted to the end of tubing 20, 21 remote from needle assembly 18. Fitting 22 shown in FIG. 1 may include a second needle assembly commonly referred to as a non-patient needle assembly (not shown), configured to be placed in communication with an evacuated blood collection tube during a blood collection procedure. The illustrated prepackaged medical device 10 includes tube holder 19 preattached to the fitting 22 and supported in the second contoured portion 17. Fittings of other configurations may be provided, as is known in the art.

Tray body 13 is typically molded unitarily from a thermoplastic material such as PVC or PETG, as indicated previously. More particularly, tray body 13 is molded into a structure as shown in FIGS. 3-9 to include a bottom wall 50 having substantially planar areas and which defines the first contoured portion 15 and the second contoured portion 17. Tray body 13 is formed further with a sidewall enclosure 51 extending generally upward from bottom wall 50. Sidewall enclosure 51 comprises lateral walls 52, 54, end walls 56, 58, and corner walls 60, 62. A peripheral flange 64 extends outwardly from sidewall enclosure 51 and defines a plane that is generally parallel to the planar areas of the bottom wall 50 and spaced from bottom wall 50 a distance that exceeds the maximum height of the needle assembly 18 as shown in FIGS. 1 and 2A.

Second contoured portion 17 is configured to depend from the bottom wall 50 in order to position and maintain tube holder 19 and fitting 22. Second contoured portion 17 includes a first recess 23 to accommodate the major body portion of the tube holder 19. The distance between the peripheral flange 64 to the bottom of first recess 23 exceeds the height of tube holder 19. The second contoured portion 17 may further have an elongated, longitudinal recess 25 to maintain and support the distal portion of the tube holder 19, fitting 22, and a portion of tubing 20, 21 associated with tube holder 19 and needle assembly 18. The major body portion of tube holder 19 may rest in the first recess 23, while a distal or forward portion of tube holder 19, fitting 22, and a portion of tubing 20, 21 is supported in elongated recess 25.

Figure 21:
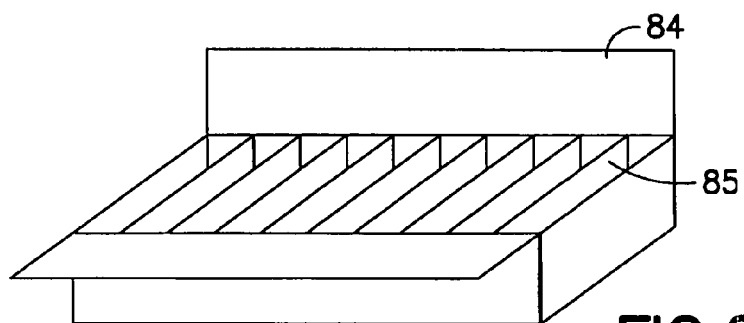
FIG. 21 is a perspective view of a case for containing two nested trays in accordance with an embodiment of the invention.
Figure 3:
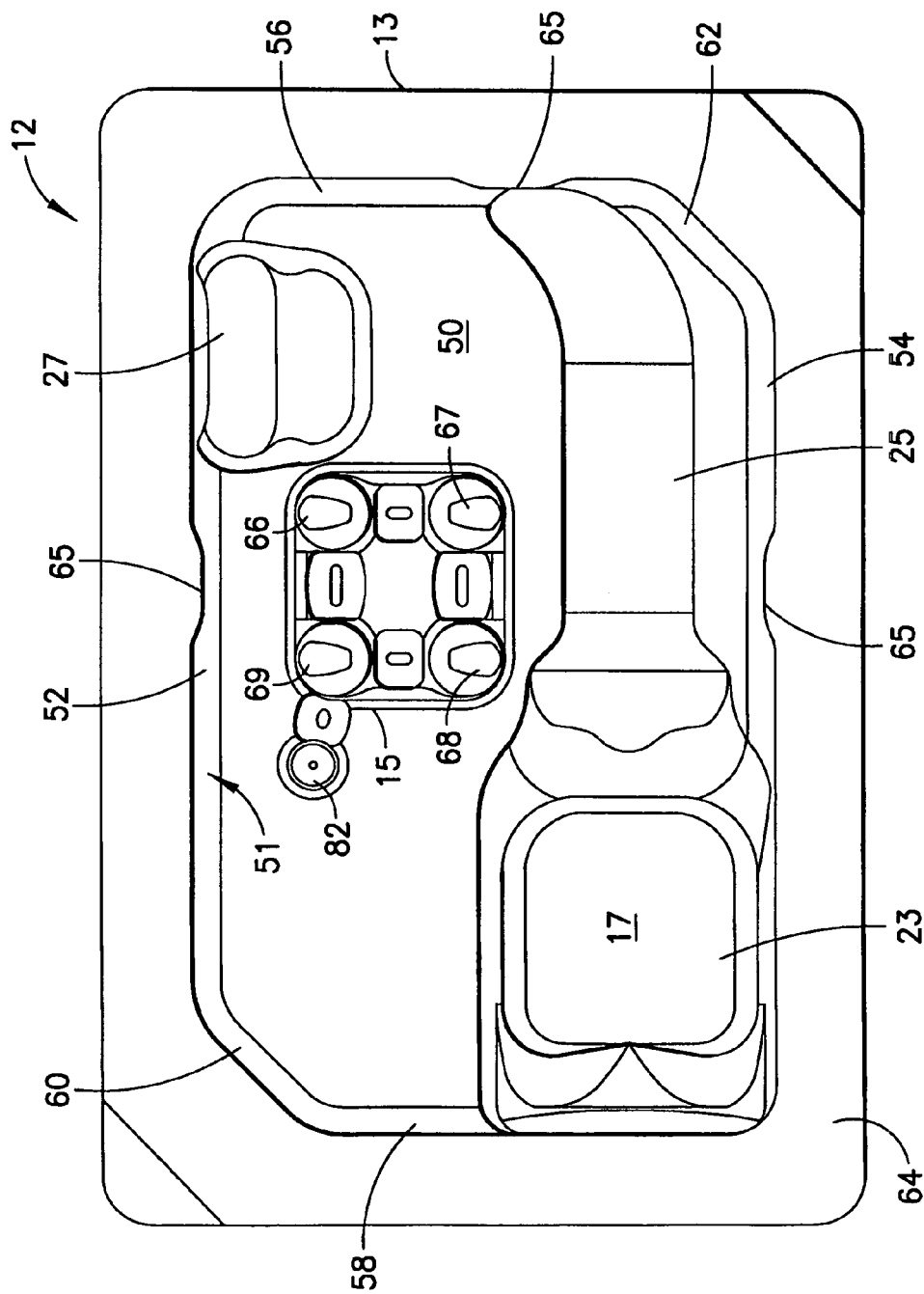
FIG. 3 is a top view of a tray of the prepackaged medical device of FIGS. 1 and 2A.
Figure 4:
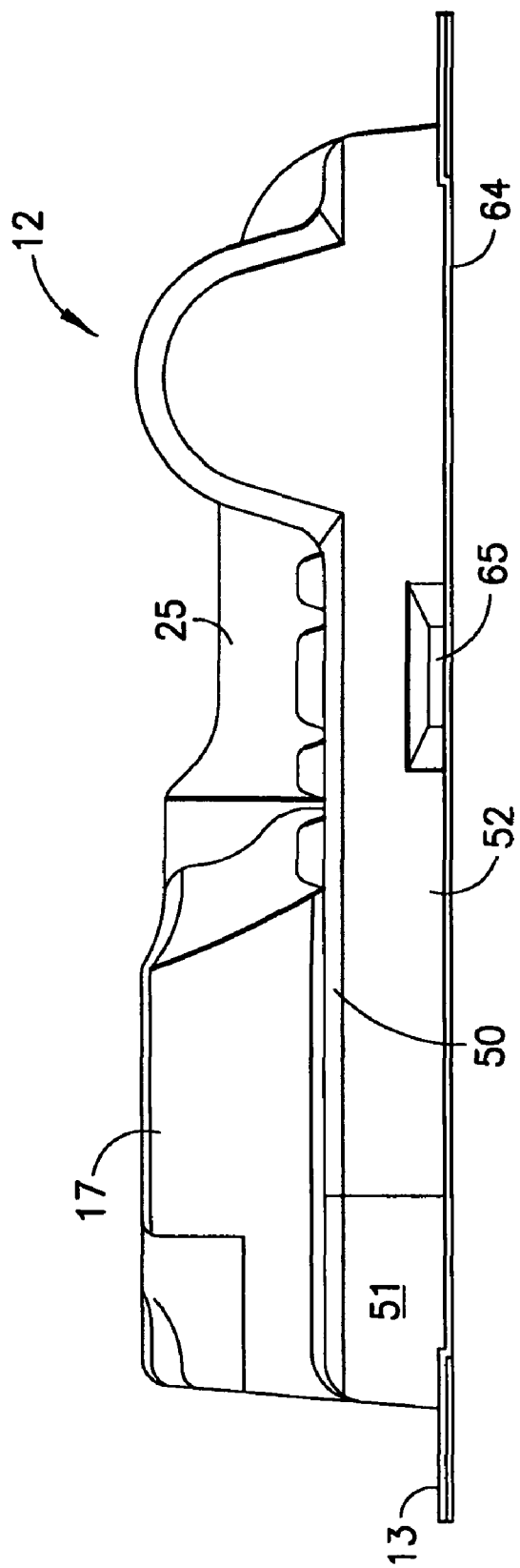
FIG. 4 is a side view of the tray of FIG. 3.
Figure 5:
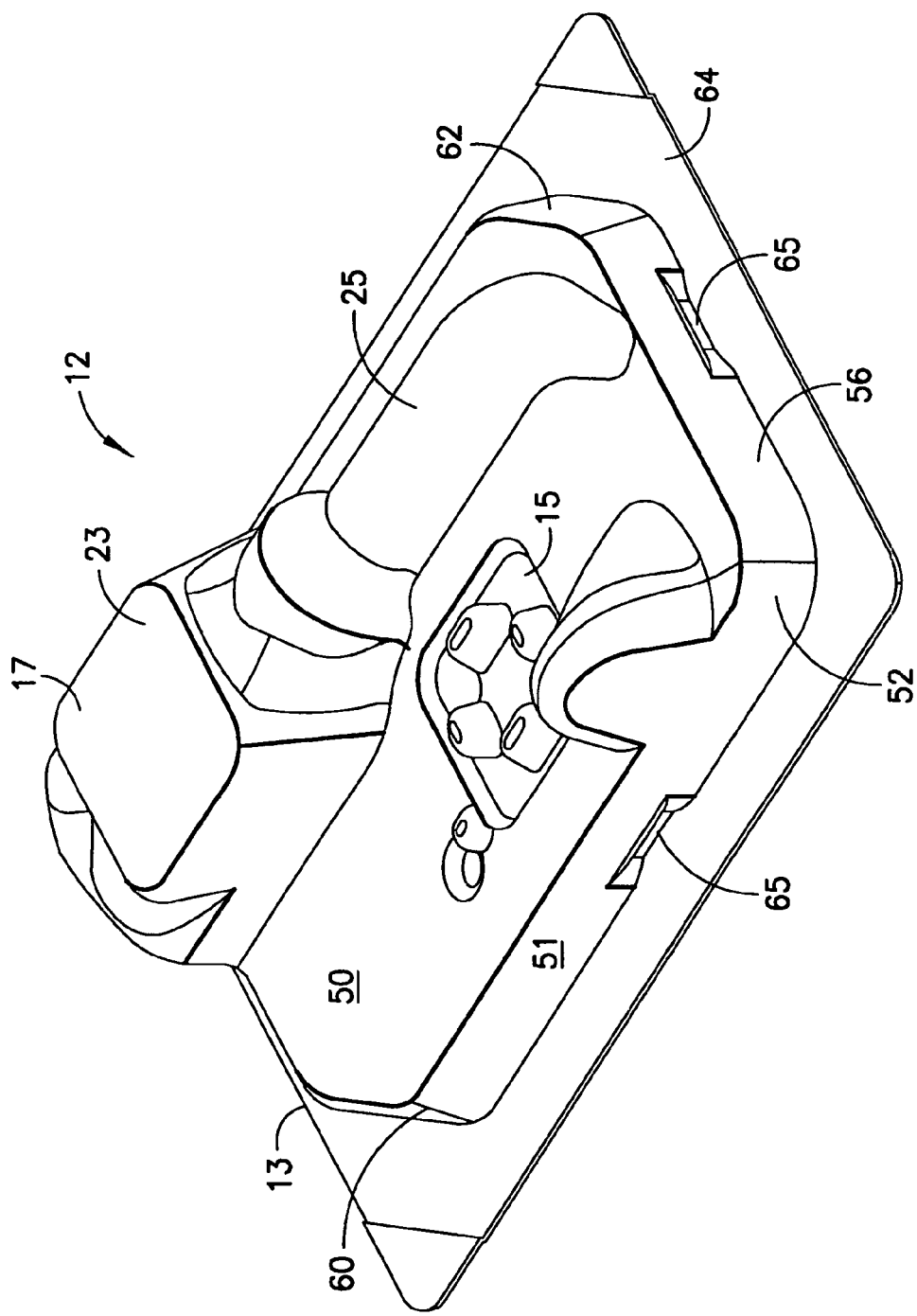
FIG. 5 is a perspective view of the bottom of the tray of FIG. 3.
Figure 6:
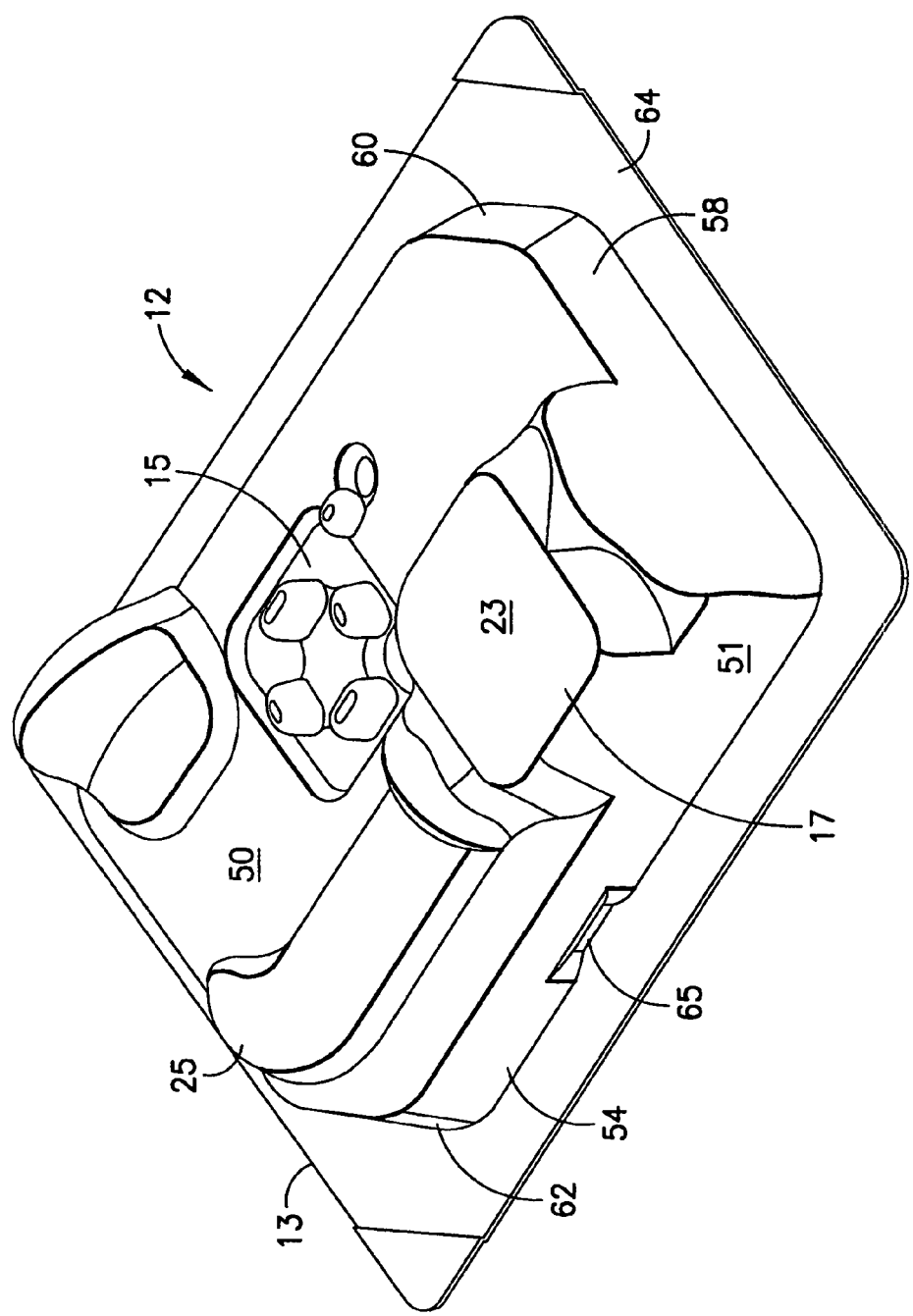
FIG. 6 is a second perspective view of the bottom of the tray of FIG. 3.
Figure 7:
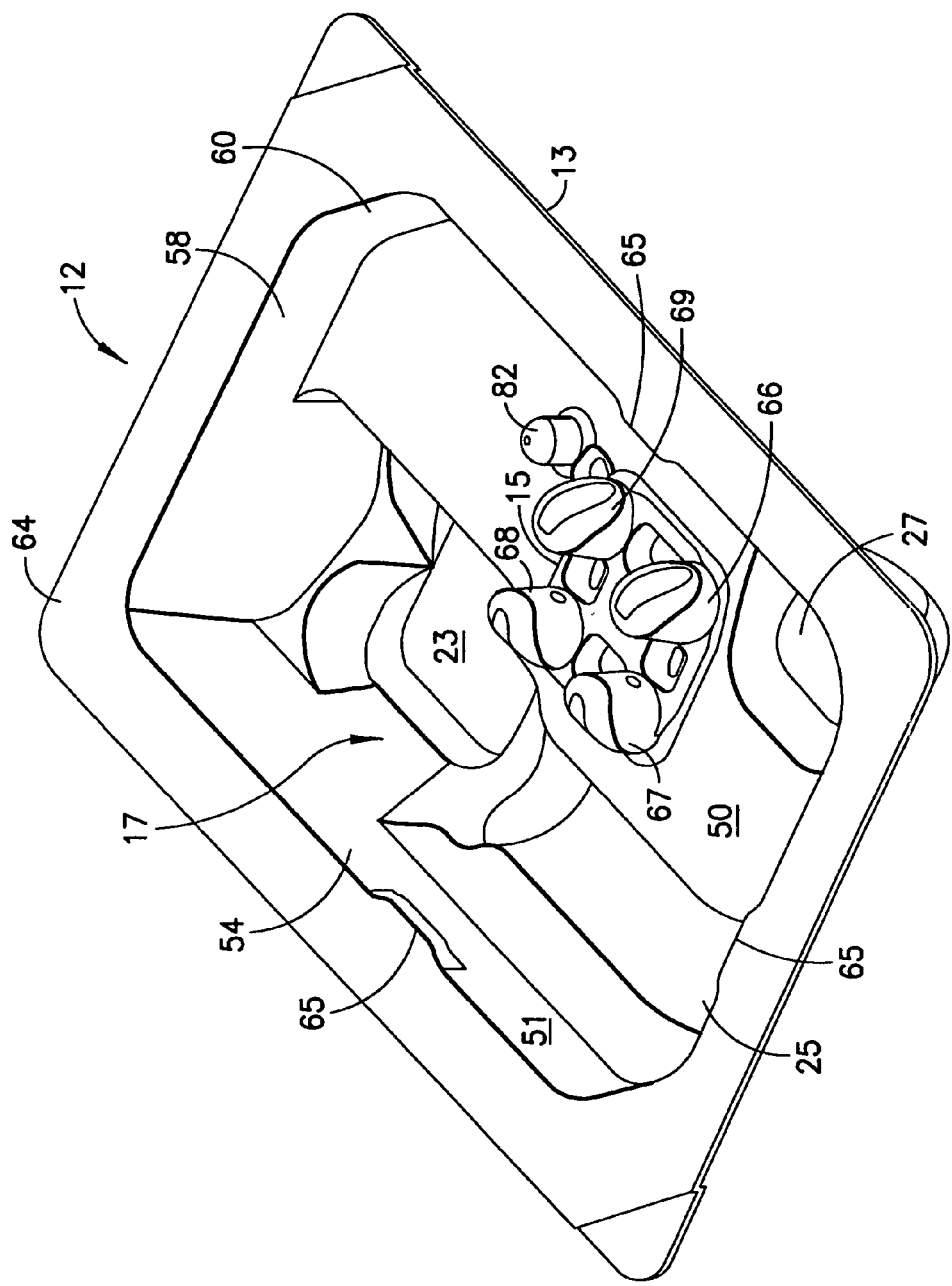
FIG. 7 is a perspective view of the top of the tray of FIG. 3.
Figure 8:
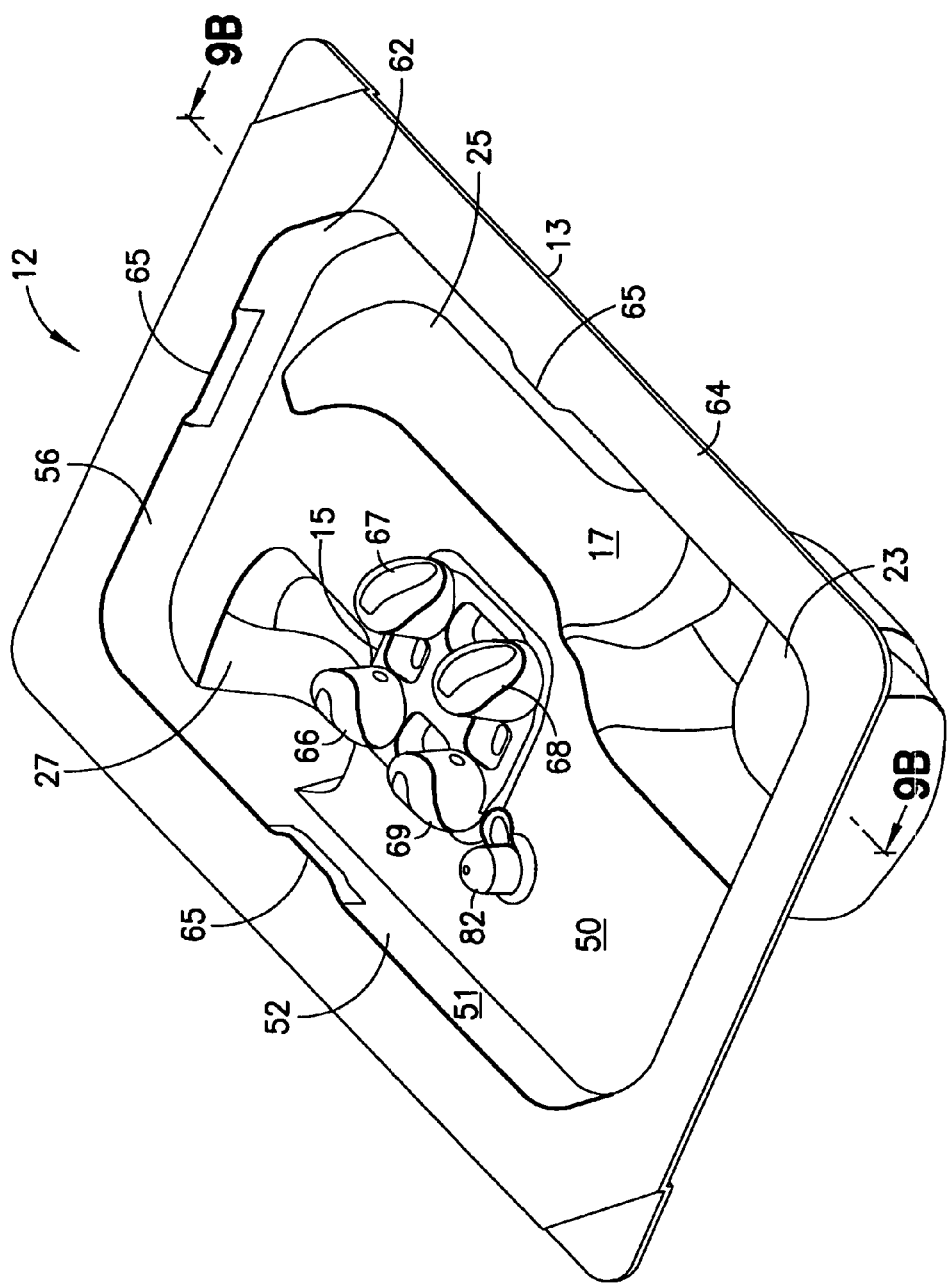
FIG. 8 is a second perspective view of the top of the tray of FIG. 3.
Figure 9:
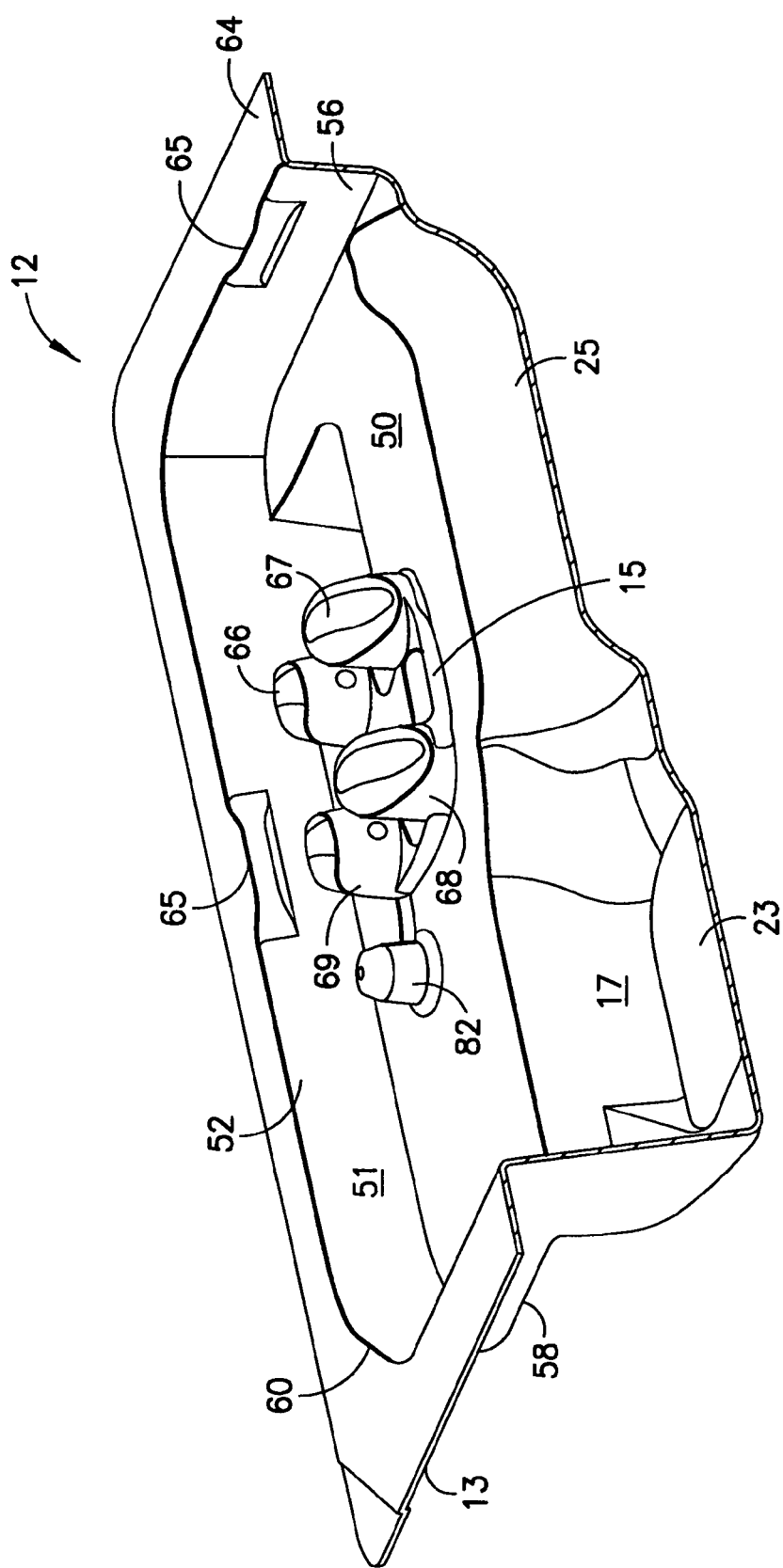
FIG. 9 is a longitudinal cross-sectional view of the tray of FIG. 3.
Figure 10:
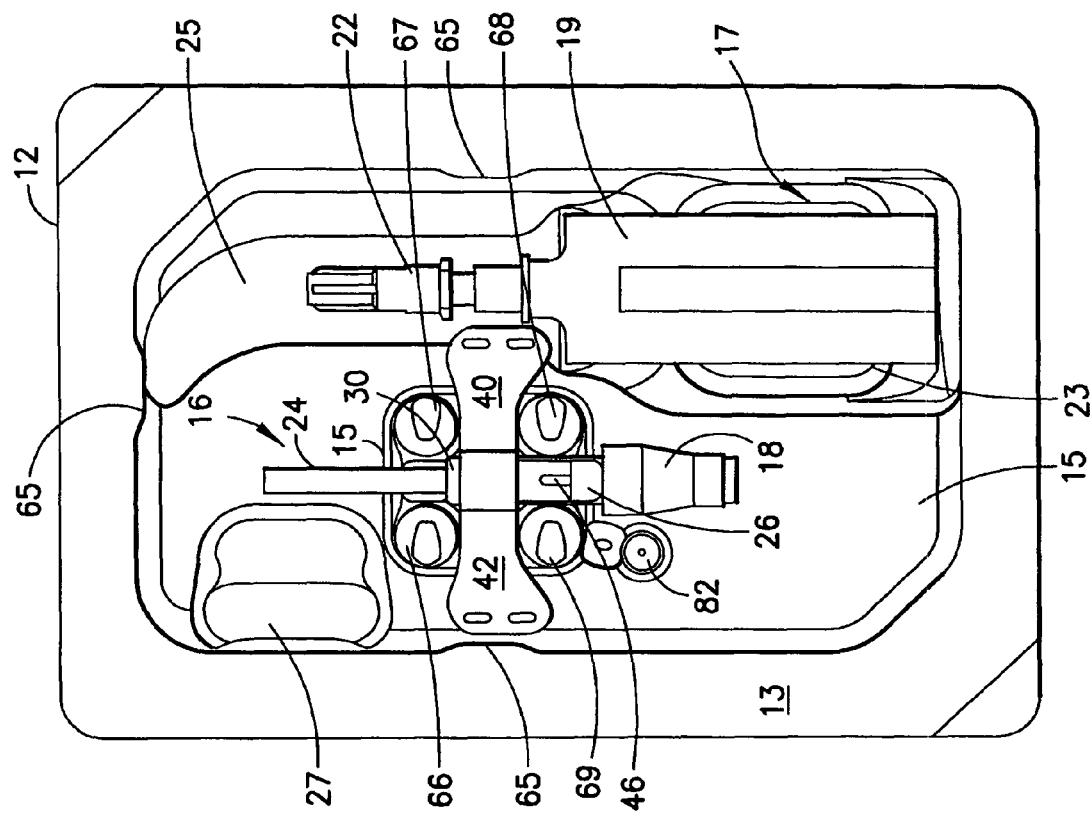
FIG. 10 is a top view of the tray of FIG. 3 supporting a medical device in the form of a blood collection set comprising a needle assembly and a tube holder, and showing the set without tubing connecting the needle assembly and tube holder.
Figure 11A:
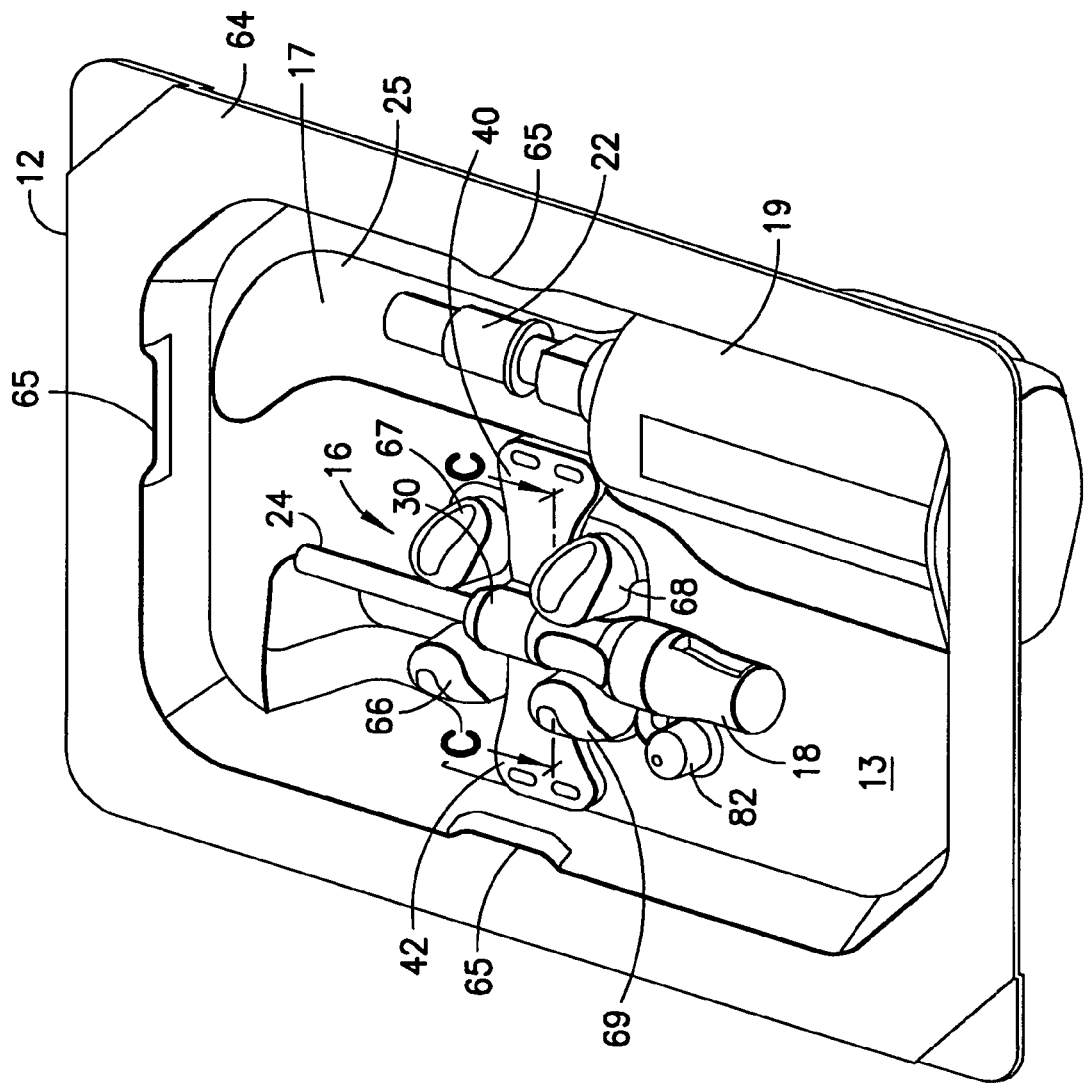
FIG. 11A is a perspective view of the tray and supported blood collection set of FIG. 10.
Figure 12:
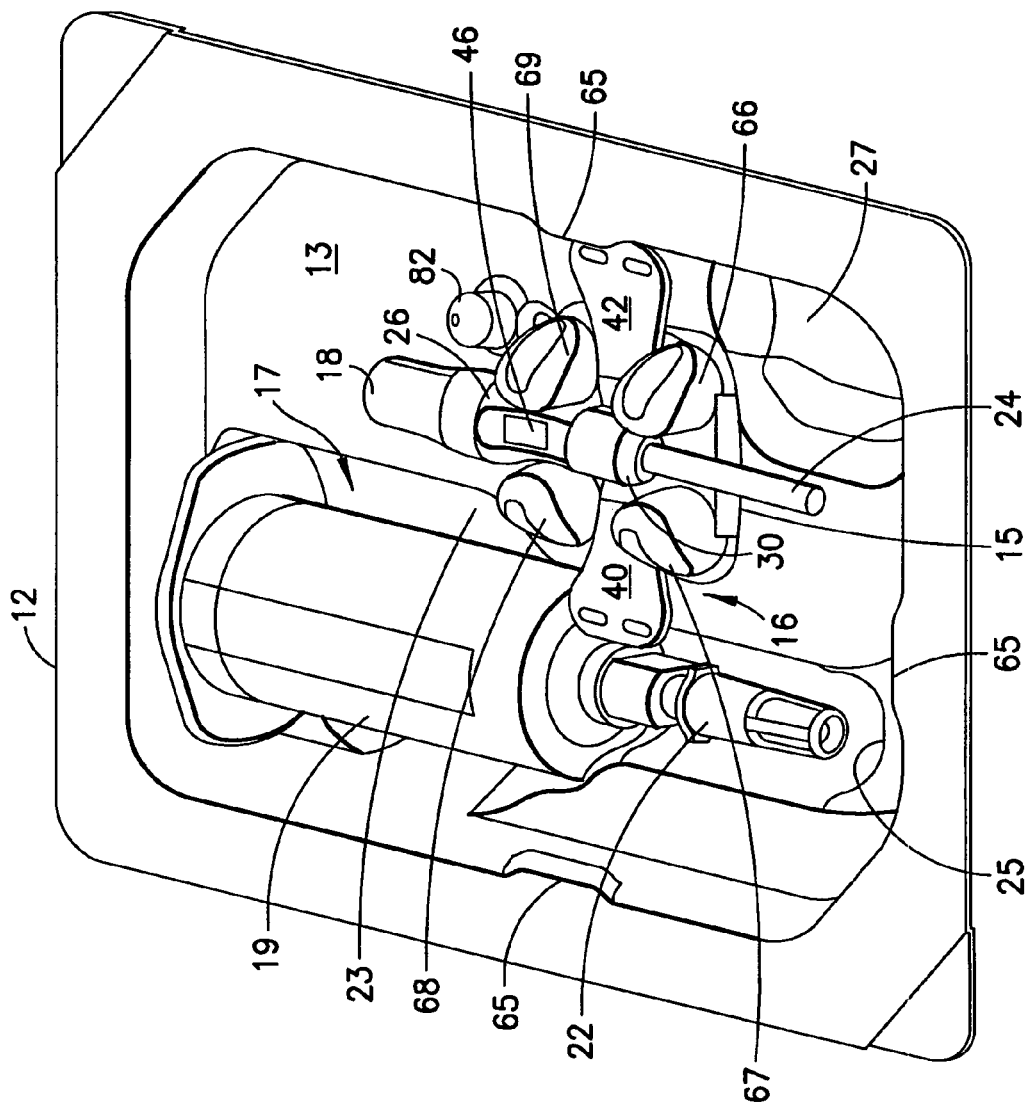
FIG. 12 is a second perspective view of the tray and supported blood collection set of FIG. 10.
Figure 13:
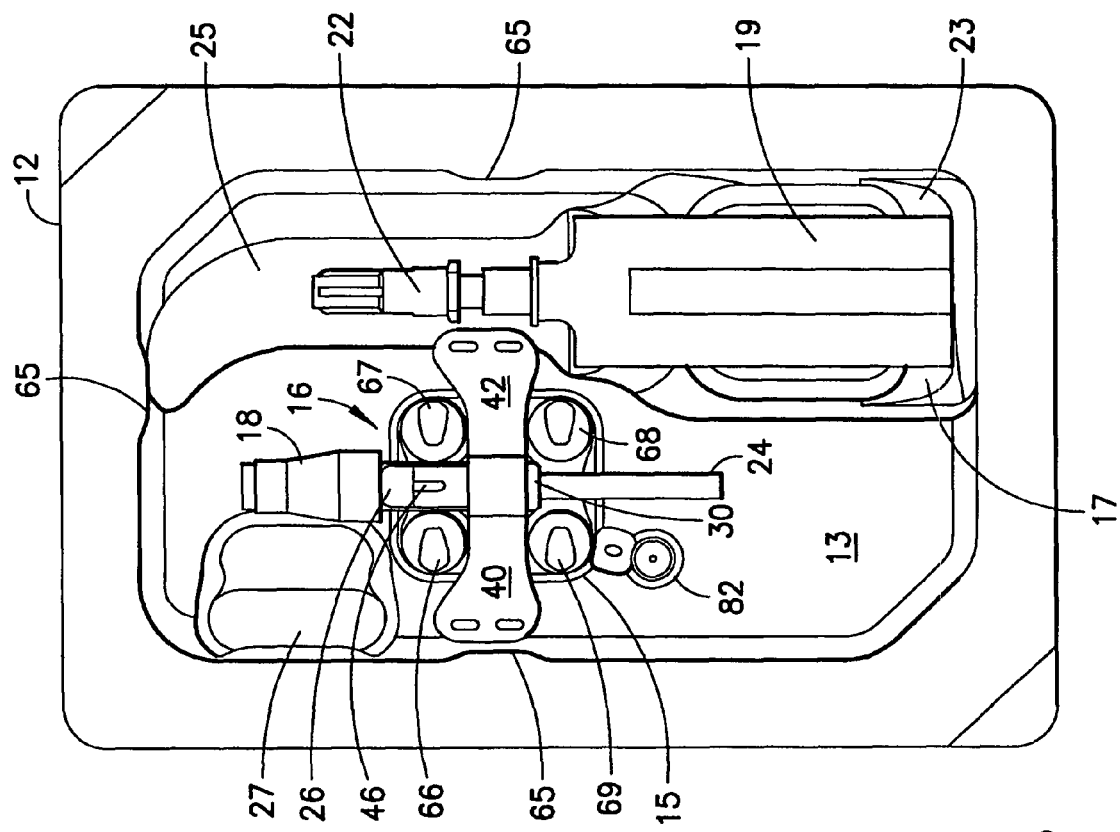
FIG. 13 is a top view of the tray and supported blood collection set of FIG. 10 showing the needle assembly in an alternative, oppositely-facing orientation in the tray.
Figure 14:
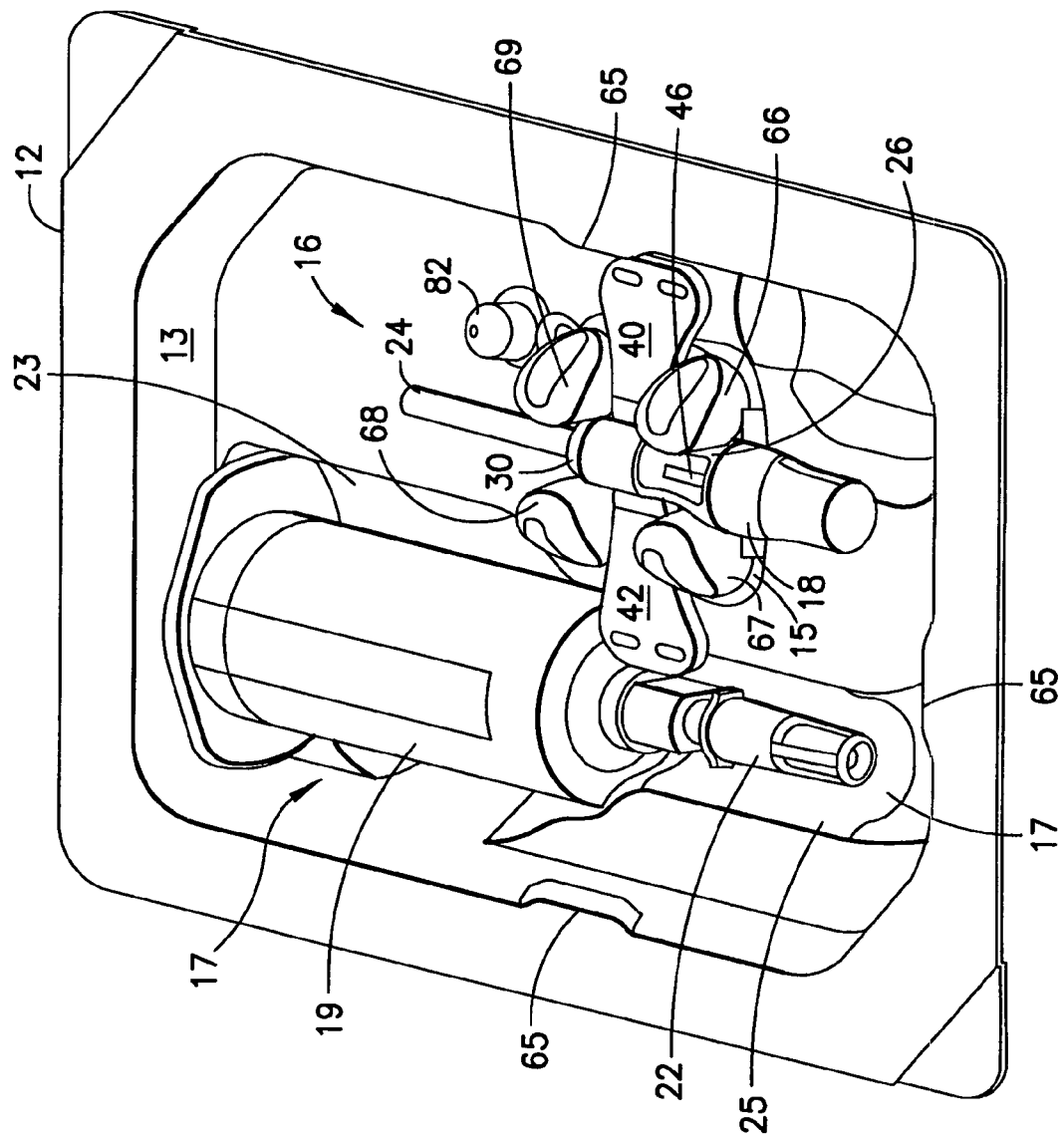
FIG. 14 is a perspective view of the tray and supported blood collection set of FIG. 13.
Figure 15:
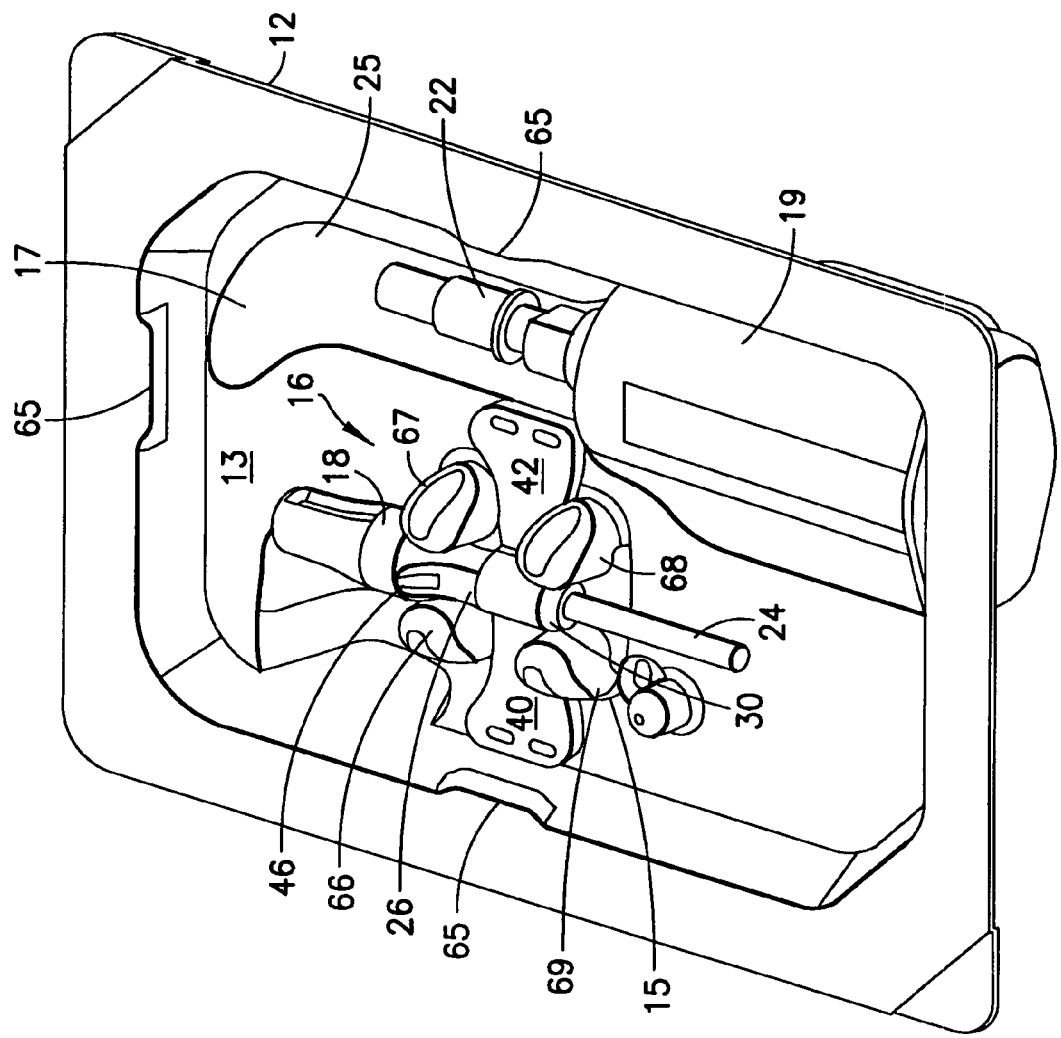
FIG. 15 is a second perspective view of the tray and supported blood collection set of FIG. 13.
Figure 16:
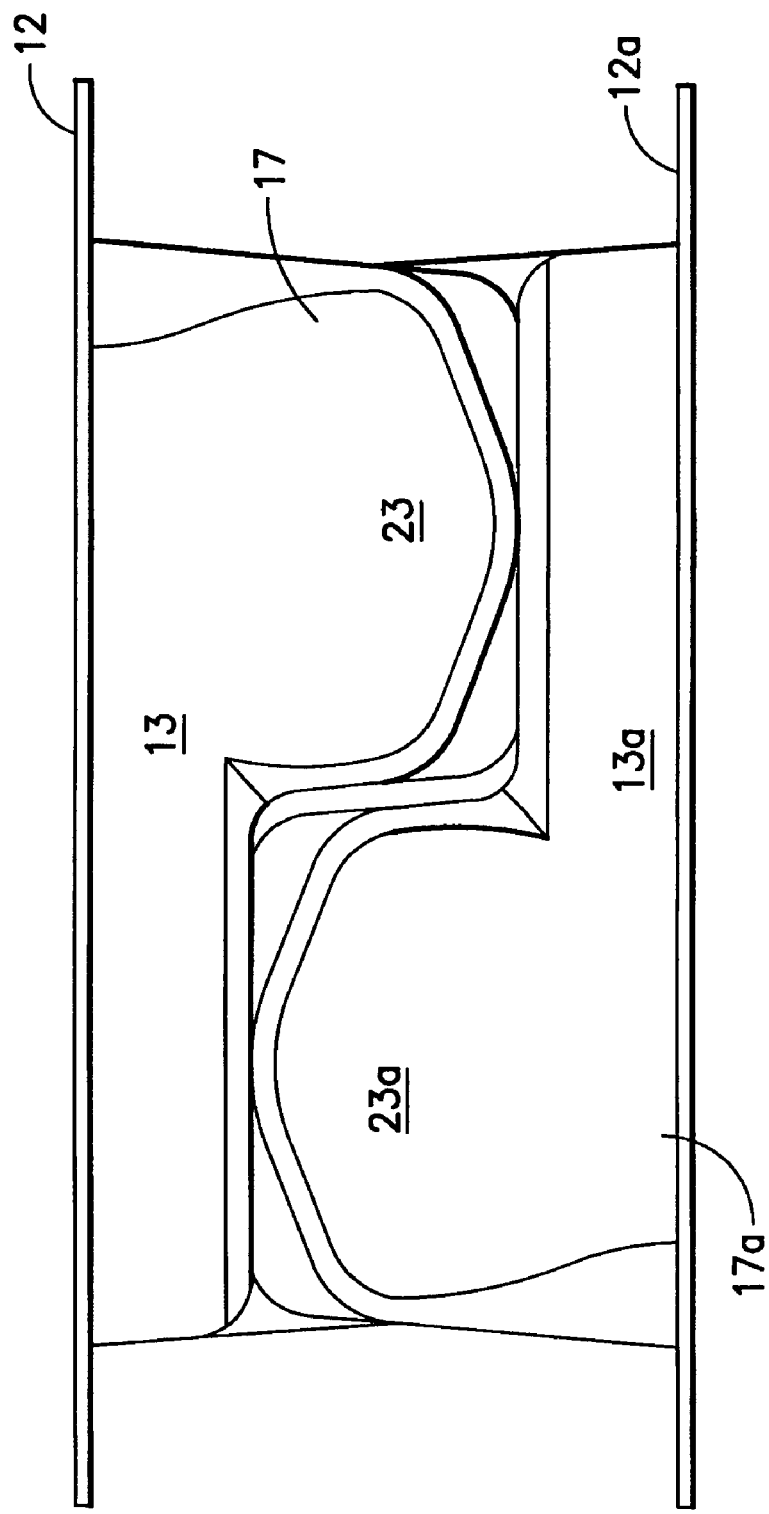
FIG. 16 is a side view showing the nesting of two trays in an embodiment of the invention.
Figure 17:
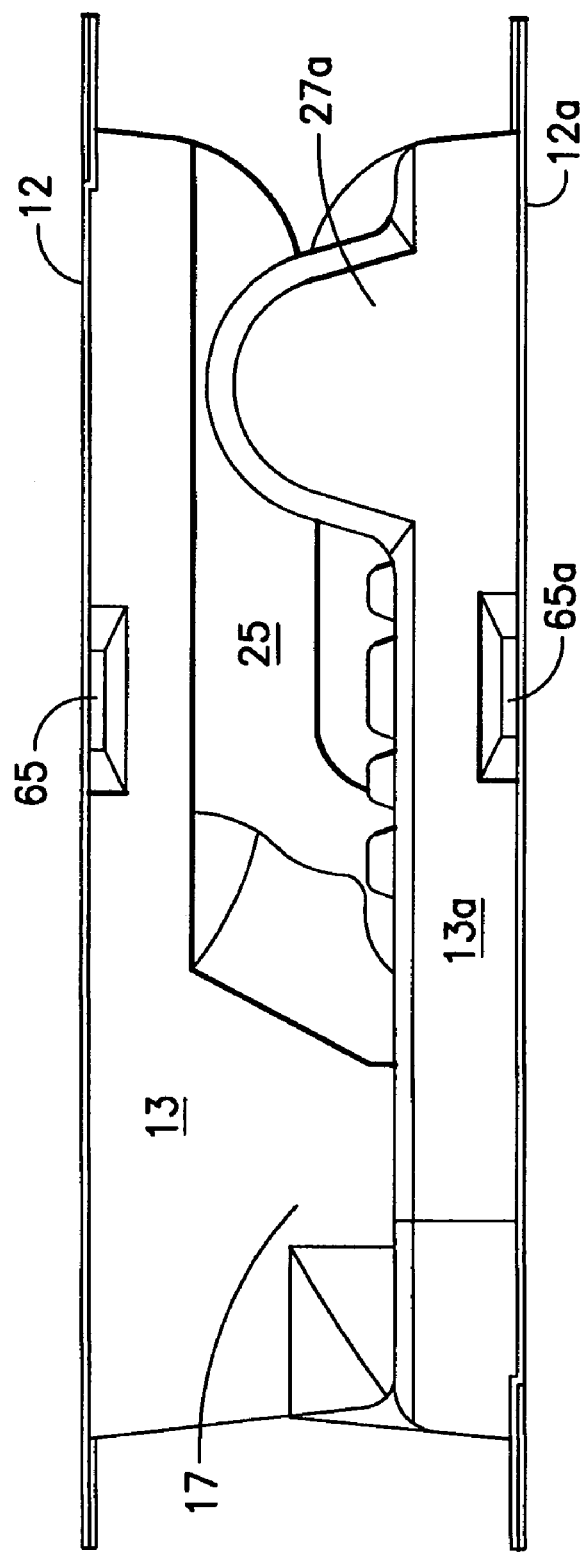
FIG. 17 is a front view of the nesting configuration shown in FIG. 16.
Figure 18:
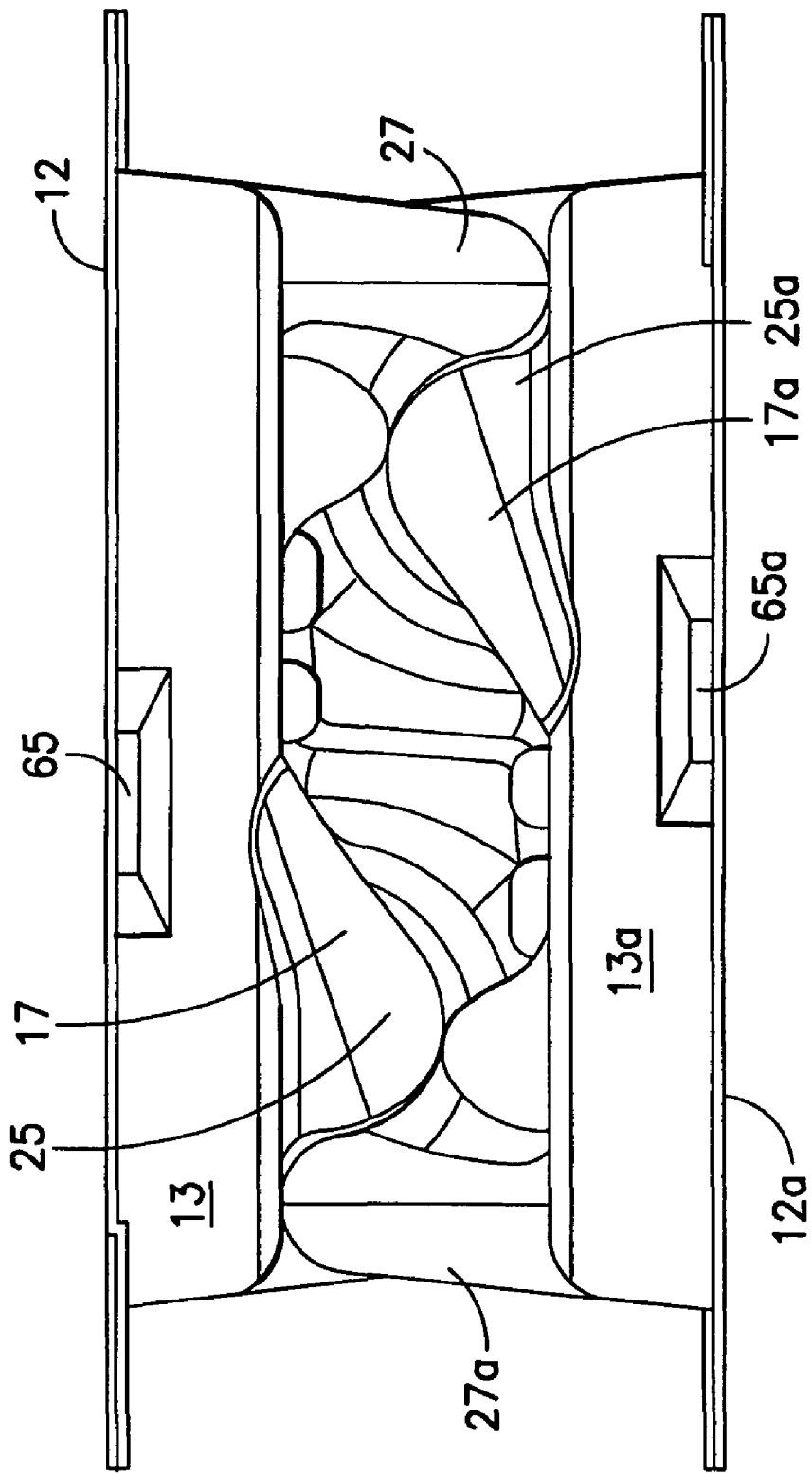
FIG. 18 is an opposing side view of the nesting configuration shown in FIG. 16.
Figure 19:
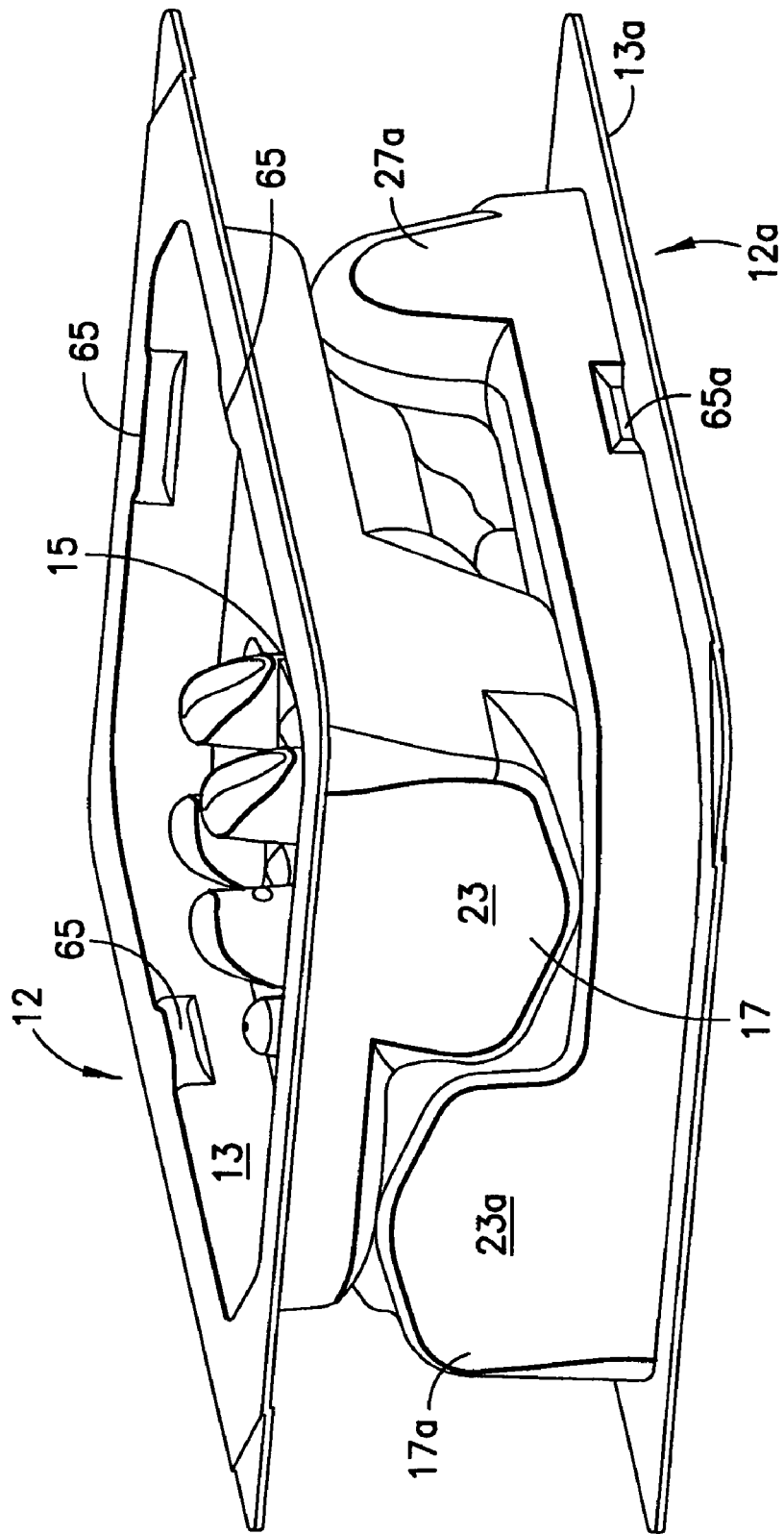
FIG. 19 is a perspective view of the nesting configuration shown in FIG. 16.
Figure 20:
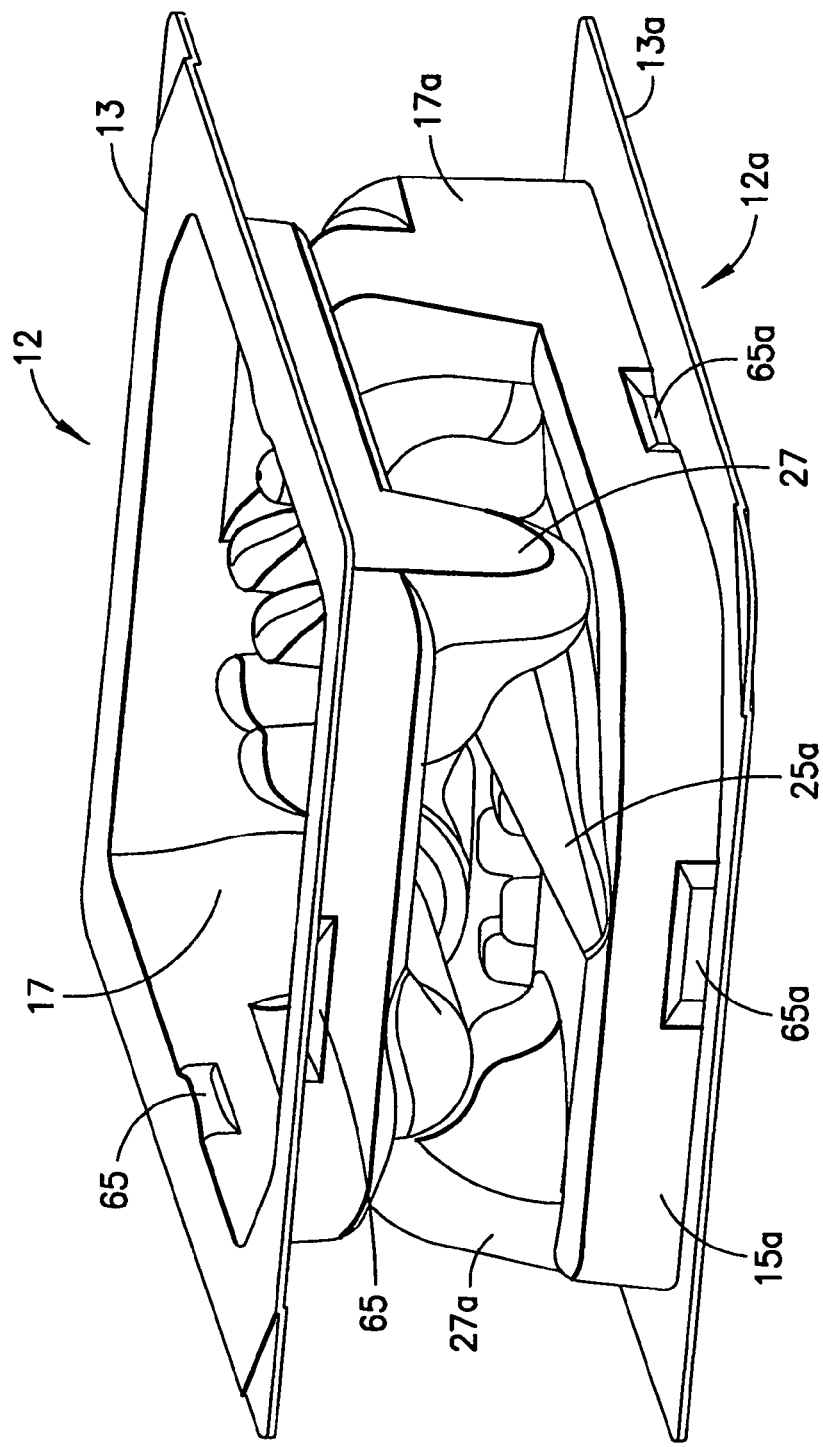
FIG. 20 is a second perspective view of the nesting configuration shown in FIG. 16.

As shown in FIGS. 3-10 tray body 13 may define a third contoured portion 27 that depends from bottom wall 50. The third contoured portion 27 is positioned opposite from the second contoured portion 17 in tray 12. As may be seen in FIGS. 16-20, the second and third contoured portions 17, 27 may be formed to allow the tray body 13 to nest with other trays 12a. The second contoured portion 17 may be positioned to engage another second contoured portion 17a, while at the opposite side of the tray body 13 the third contoured portion 27 contacts the bottom wall 50a of the other tray 12a. With two trays 12 and 12a nested in this manner, the overall thickness of the nested arrangement is slightly greater than the thickness of a single tray, but is less than the thickness of two separate trays. For example, if the thickness of a single tray is defined by Y, and the overall thickness of two nested trays (such as arranged in FIGS. 16-20) is defined by Z, then a nested configuration of two trays can be exemplified through a formula in which $Y \leq Z < 2Y$. This arrangement also provides structural rigidity and allows multiple sets of trays 12, 12a to be easily nested together and packaged within a shipping container 84 as shown in FIG. 21, with two nested trays 12, 12a being located in each compartment 85 of the container 84 in this embodiment of the shipping container 85. Also, when two trays are in such a nested relationship, rotational movement of one tray 12 with respect to the other tray 12a is prevented, thereby facilitating packaging and handling. Additionally, the opposed locations of the second and third contoured portions 17, 27 allow the tray body 13 to stand stable on any generally flat or planar surface, such as an examination table, to aid the user in removing lid 14 and the blood collection set 16. Desirably, the second and third contoured portions 17, 27 extend from the bottom wall 50 of the tray body 13 such that a plane extending across bottom portions of the second and third contoured portions 17, 27 is generally parallel with the bottom wall 50 of the tray body 13.

Portions of peripheral flange 64 may be undercut to define inward-extending lips 65 adjacent lateral walls 52, 54, 56, 58. Theses lips 65 may define concave regions at locations on lateral walls 52, 54, 56, 58 between bottom wall 50 and peripheral flange 64. The concave regions may be configured dimensionally to grip a section of tubing 20, 21 as shown in FIGS. 1 and 2A to maintain tubing 20, 21 in the internal space defined by tray body 13.

A plurality of posts 66-69 project upwardly from bottom wall 50 at locations spaced from one another and spaced from the sidewall enclosure 51. As may be seen in the Figures, one embodiment includes four posts 66-69 arranged in the general location wherein the needle assembly 18 is to be received (e.g., the first contoured portion 15). Thus, the posts 66-69 are generally located in the first contoured portion 15. The top of each of the posts 66-69 may be substantially coplanar with peripheral flange 64. Posts 66-69 are characterized by opposed facing walls spaced from one another such that portions of needle assembly 18, typically the needle hub and wings 40, 42 extending from safety shield 26, are engaged by at least two opposing posts 66-69. Posts 66-69 may further include non-gripping sidewalls oriented at acute angles relative to bottom wall 50. Thus, posts 66-69 may taper to smaller cross sections at locations further from bottom wall 50. The tapered configuration of posts 66-69 are resistant to deformation in response to downward compressive forces on the tray body 13.

Figure 11B:
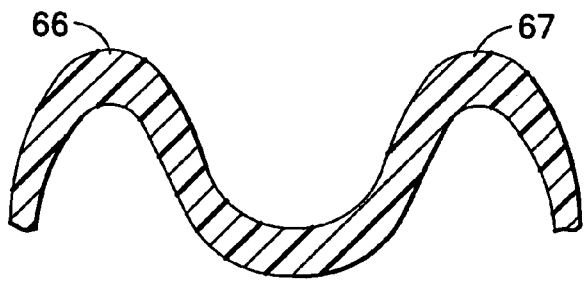
FIG. 11B is a cross-sectional view taken along line C-C in FIG. 11A of a pair of posts upstanding from a bottom wall of the tray of FIG. 11A, shown without the needle assembly in place therebetween.
Figure 11C:
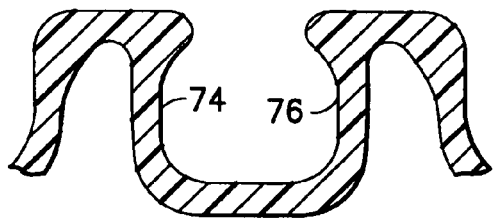
FIG. 11C is a cross-sectional view of an alternative configuration of the posts shown in FIG. 11B.

Another example of posts 66-69 is illustrated in cross-section in FIG. 11C, wherein the facing walls of one or more posts has opposed convex inner walls 74, 76. The opposed convex inner walls 74, 76 may grip the needle assembly 18 and/or the wings 40, 42, for example, by extending around the periphery of the needle assembly 18, typically at least 50% of the perimeter of the needle assembly 18, to substantially engage the top end or portion of the needle assembly 18. This configuration facilitates the inward resilient deflection or dimpling of these convex walls, and hence secure resilient gripping of needle shield 26 and/or wings 40, 42. Posts 66-69 may be configured in the manner provided in Unites States application Ser. No. 10/229,740 entitled "Packaging For Push Button Blood Collection Set", the disclosure of which is incorporated herein by reference in its entirety.

Figure 2B:
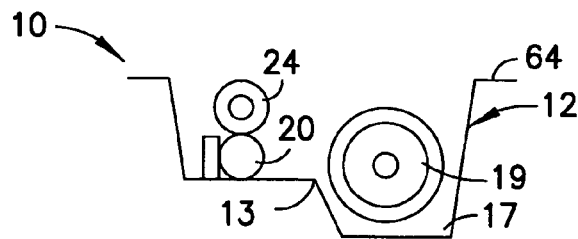
FIG. 2B is a simplified cross-sectional illustration of the general orientation of the elements of FIG. 2A.

Tray 12 is further characterized by a positioning post 82 that projects from bottom wall 50 of tray body 13 at a location spaced from posts 66-69. Positioning post 82 has a top portion that is located below the plane defined by peripheral flange 64. In order to achieve desired positioning of the blood collection set 16 in tray 12, positioning post 82 is useful in preventing tubing 20 of longer length from becoming repositioned from underneath safety cap 24 (or needle cannula therein in another embodiment) as shown in FIGS. 2A and 2B. Thus, positioning post 82 maintains the correct positioning of longer length tubing 20 relative to the needle assembly 18. As shown in FIG. 1, post 82 may not be necessary with shorter lengths of tubing such as tubing 21.

The prepackaged medical device 10 is generally packaged in opposite order from the order in which the blood collection set 16 is to be removed from the packaging. Additionally, the relative opposed locations of the first and second contoured portions 15, 17 on opposite sides of tray body 13 facilitate both packaging of blood collection set 16 in tray 12 and safe and organized unloading of the blood collection set 16. In particular, the opposed locations of the first and second contoured portions 15, 17 directs the user to remove the blood collection set 16 in a specific order to minimize the possibility of inadvertent actuation of the needle assembly 18. To assemble the prepackaged medical device 10, the tube holder 19 may be positioned in the second contoured portion 17. The fitting 22 may be preattached to the tube holder 19 and may be positioned within the elongated recess 25 at the same time the tube holder 19 is placed in the first recess 23. Depending upon the length of tubing 20, 21, tubing 20, 21 may require multiple windings. Needle assembly 18 of blood collection set 16 may be mounted in tray 12 in two opposite directions orientations as shown in FIG. 2A and FIG. 1 depending upon the length of tubing 20, 21 used, respectively. If a longer length of tubing, for example, tubing 20, is used, the needle assembly 18 may require a position wherein the needle assembly 18 is orientated in a direction opposite to the orientation of tube holder 19, while when shorter tubing, for example, tubing 20, is used the needle assembly 18 may face the same direction as the tuber holder 19.

When longer length tubing 20 is used in the blood collection set 16 additional structure may be utilized to ensure that tubing 20 does not interfere with removal of the needle assembly 18 and tube holder 19. Tubing 20, as shown in FIG. 2A, extends from the fitting 22 associated with tube holder 19, is coiled within tray body 13 adjacent bottom wall 50, and passes between post 82 and first contoured portion 15, and is finally connected to the needle assembly 18. Tubing 20 is restrained vertically in tray body 13 by lips 65 on opposing sides of peripheral flange 64, and eventually passes between positioning post 82 and post 69. Thus, lips 65 assist in retaining tubing 20 in tray body 13 without a separate band wrapped directly around the tubing. Additionally, the tubing 20 is further restrained in place by placing a portion of needle assembly 18, namely safety cap 24 or even the needle cannula, over top of the portion of tubing 20 forward or distal of the portion of the tubing 20 passing between post 82 and first contoured portion 15, specifically post 69. Accordingly, when the needle assembly 18 is placed into tray 12, the safety cap 24 covering the needle cannula, or the needle cannula alone if desired, will further restrain tubing 20 against the bottom wall 50 of the tray body 13 by direct engagement therewith. By restraining tubing 20 below safety cap 24 or needle cannula, the tubing 20 is further prevented from uncoiling above flange 64, and is protected from damage by the needle cannula and safety cap 24 or safety shield 26 during removal of the needle assembly 18 from tray 12 as the needle assembly 18 lies over top of the tubing 20.

The needle assembly 18 may be placed in tray 12 by urging the narrowed portion of safety shield 26 and wings 40, 42 into the plus sign shaped space defined by posts 66-69. The necked down portion of safety shield 26 is aligned with the space between posts 66-69. The opposed surfaces of posts 66-69 will position needle assembly 18 substantially adjacent bottom wall 50 of tray 12 in the desired position. In this position, wings 40 and 42 will be substantially adjacent and parallel to bottom wall 50. As indicated, when longer tubing 20 is used, the needle assembly 18 traps at least a portion of the tubing 20 against bottom wall 50 of tray body 13.

The prepackaged medical device 10 is completed by applying lid 14 to peripheral flange 64. Lid 14 is adhered or bonded removably to peripheral flange 64. Lid 14 is supported around its periphery by peripheral flange 64. Additionally, central portions of lid 14 may be supported by the tops of posts 66-69.

Bottom wall 50 of tray 12 and central portions of lid 14 are relatively flexible and may be moved toward one another in response to pressure applied thereto. However, posts 66-69 are relatively rigid and resist forces that would urge central portions of lid 14 toward bottom wall 50 of tray 12. Additionally, posts 66-69 are disposed on opposite respective sides of actuator button 46 and project from bottom wall 50 a distance greater than the maximum height of needle assembly 18. Hence, posts 66-69 prevent inadvertent actuation of safety shield 26 that could make blood collection set 16 unusable. Additionally, posts 66-69 releasably position and maintain needle assembly 18 at a desired position within tray 12, and therefore prevent any movement that might cause safety cap 24 of the needle cannula, if exposed, to project through cover 14.

Positioning post 82 does not perform a direct holding function for the blood collection set 16. However, positioning post 82 facilitates spooling of longer length tubing 20 and limits damage to longer length tubing 20 during shipping and handling and removal of the blood collection set 16, as described previously.

Blood collection set 16 may be accessed merely by peeling lid 14 from peripheral flange 64 substantially in a conventional manner for blister packages. A user then grips portions of needle assembly 18 near proximal end 28 of safety shield 26 and lifts needle assembly 18 upwardly away from bottom wall 50 allowing a removal of the needle assembly 18. When the needle assembly 18 is removed from the tray 12, the tubing 20, 21 will then be released, followed by fitting 22 and tube holder 19. Fitting 22 and tube holder 19 are removed from the second contoured portion 17 in substantially simultaneous fashion. The blood collection set 16 may then be used in a conventional manner.

While the prepackaged medical device 10 is herein described with tubing 20, 21 of twelve inches in length and seven inches in length, respectively, these are merely exemplary embodiments. The blood collection set 16 may be used with lengths of tubing 20, 21 of substantially any length. The lips 64 on tray body 13, post 82, and needle assembly 18 itself provide structure for restraining tubing 20, 21 of increasing length wherein coiling of such longer tubing 20, 21 could cause the tubing 20, 21 to project out of the tray body 13 when the lid 14 is removed due to the tension force induced in the tubing 20, 21 during the coiling process.

FIGS. 22-25 depict further embodiments of the present invention that include many components which are substantially identical to the components of FIGS. 1-21. Accordingly, similar components performing similar functions will be numbered identically to those components of FIGS. 1-21, except that a suffix "b" will be used to identify those similar components in FIGS. 22 and 23, and a suffix "c" will be used to identify those similar components in FIGS. 24 and 25.

Figure 22:
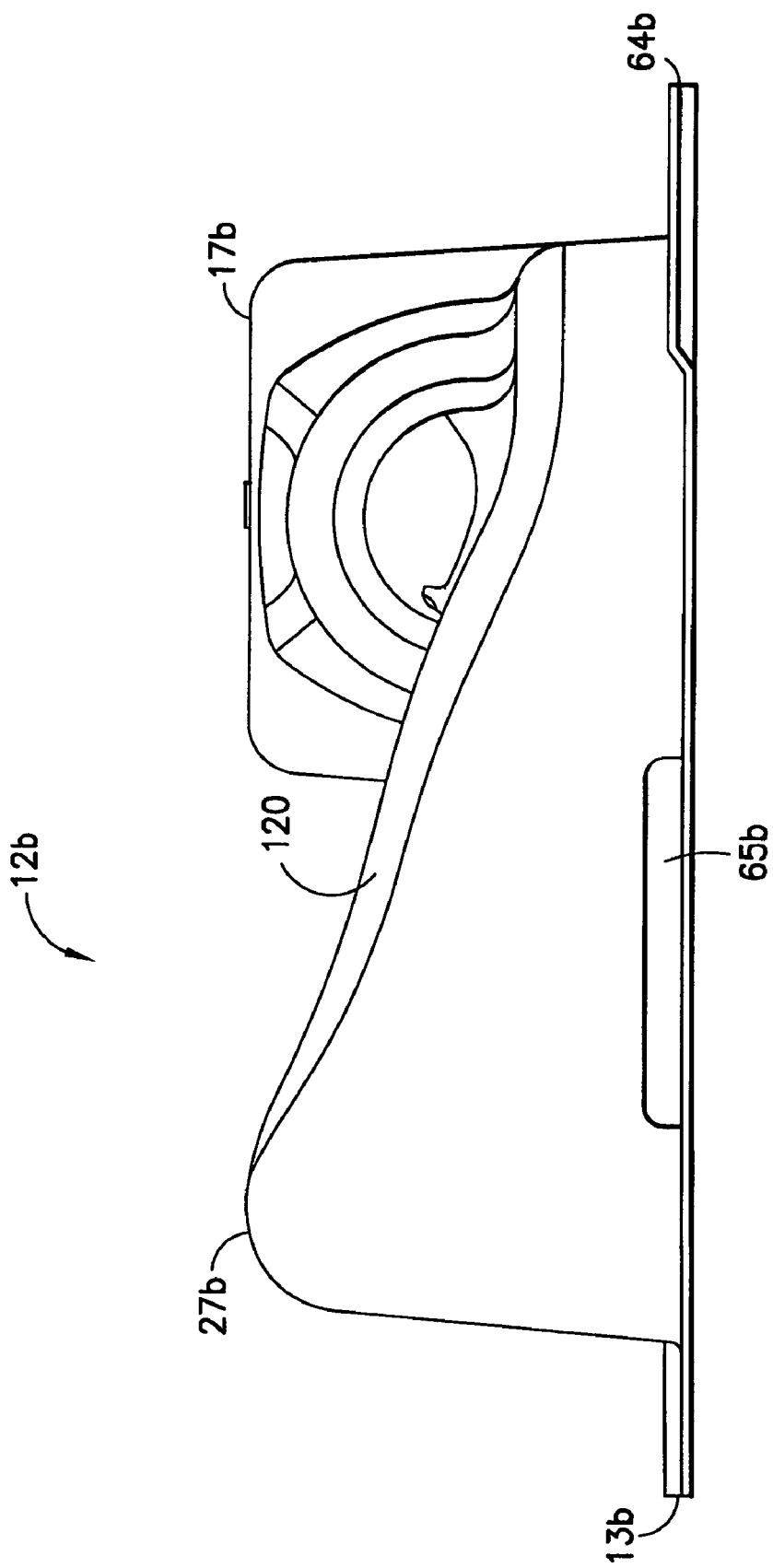
FIG. 22 is a front view of a tray in an alternate embodiment of the invention.
Figure 23:
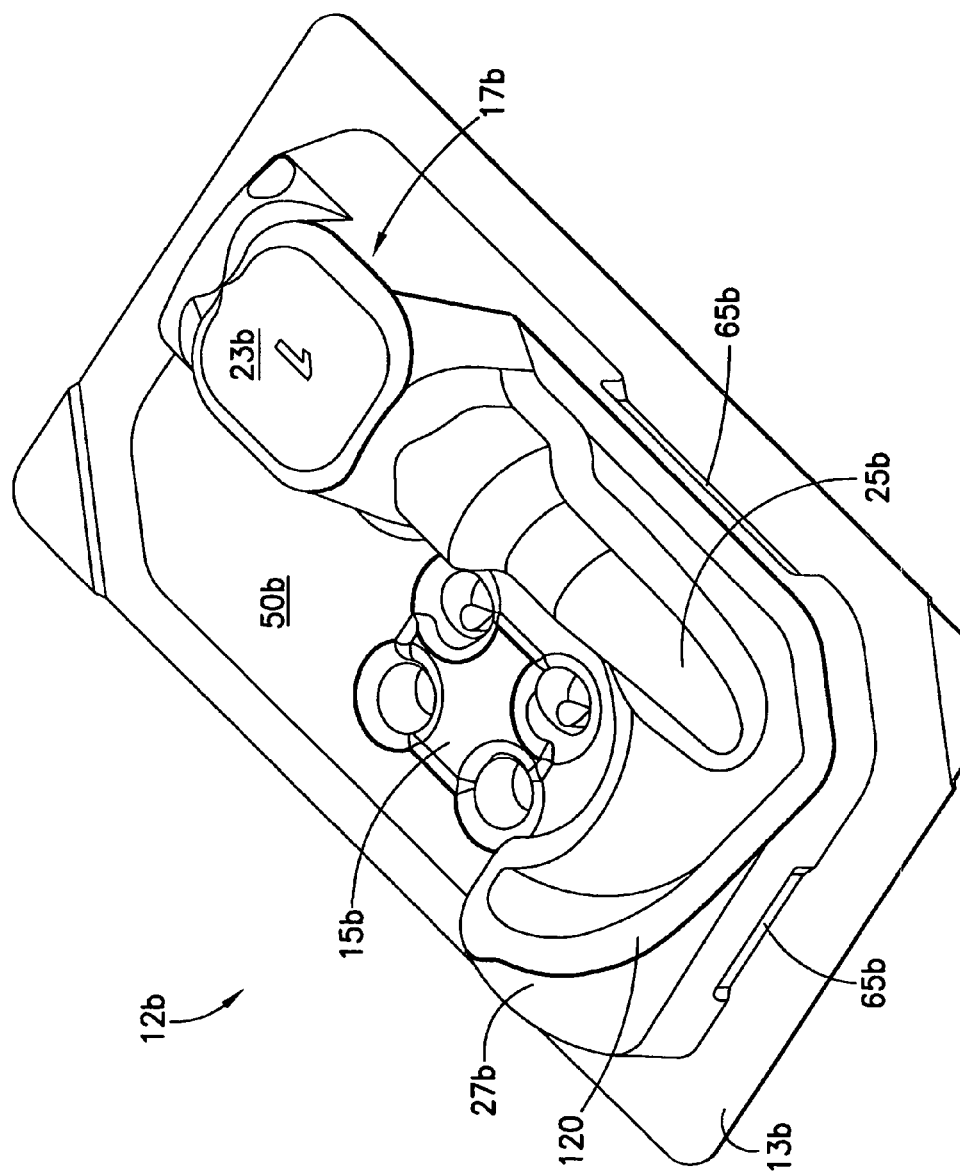
FIG. 23 is a perspective view of the bottom of the tray of FIG. 22.

In the embodiment depicted in FIGS. 22-23, tray body 13b of tray 12b is substantially identical to that discussed above. For example, tray body 13b includes a bottom wall 50b, with first contoured portion 15b depending therefrom for accommodating a needle assembly of a blood collection set, and with a second contoured portion 17b depending therefrom and including a first recess 23b for accommodating the major body portion of a tube holder. An elongated recess 25b also depends from bottom wall 50b, for maintaining and supporting the distal portion of the tube holder, as well as a distal or forward portion of the tube holder, the fitting, and any tubing attached thereto. A third contoured portion 27b also depends from bottom wall 50b at a position opposite from the second contoured portion 17b. Portions of the tray body 13b are undercut at inward-extending lips 65b, which are dimensionally configured to grip a section of the tubing in order to maintain the tubing within the internal space defined by tray body 13b prior to use of the device, in a similar manner as described above. In the embodiment of FIGS. 22-23, a ramped portion 120 extends between the elongated recess 25b of second contoured portion 17b and third contoured portion 27b. Such a ramped portion 120 provides effective space and support within the internal spaced defined by tray body 13b to accommodate the tubing extending between the tube holder and the needle assembly when a medical device is packaged within tray 12b. As seen in FIG. 22, the bottom portions of second contoured portion 17b and third contoured portion 27b extend from the bottom surface defined by bottom wall 50b to positions in which a plane extending across the bottom surfaces of the second and third contoured portions 17b, 27b is generally parallel with peripheral flange 64b and/or the bottom wall 50b of the tray body 13b.

Figure 24:
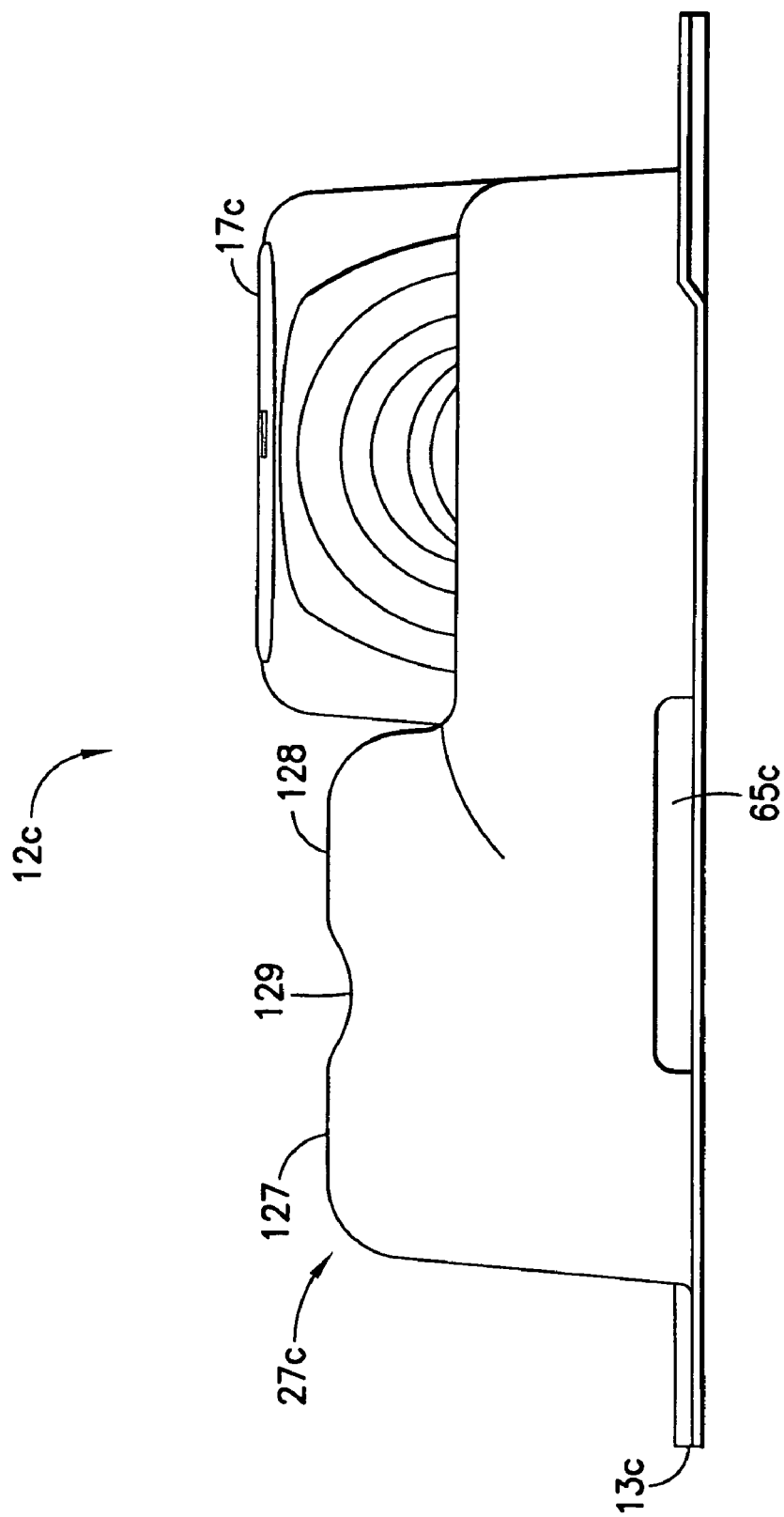
FIG. 24 is a front view of a tray in a further embodiment of the invention.
Figure 25:
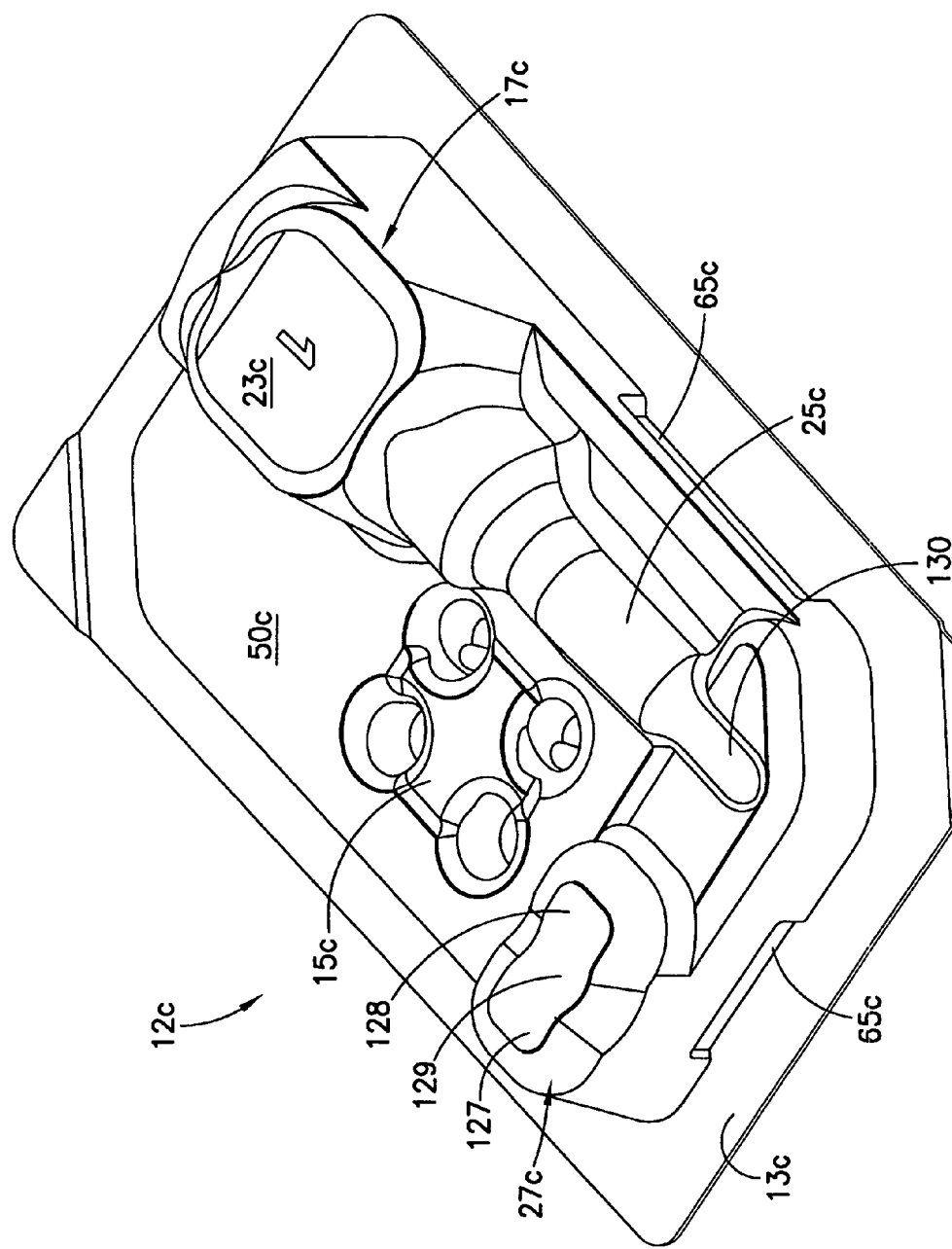
FIG. 25 is a perspective view of the bottom of the tray of FIG. 24.

FIGS. 24-25 depict a further embodiment of tray 12c, including tray body 13c having a bottom wall 50c, with first contoured portion 15c depending therefrom for accommodating a needle assembly of a blood collection set, and with a second contoured portion 17c depending therefrom and including a first recess 23c for accommodating the major body portion of a tube holder. An elongated recess 25c also depends from bottom wall 50c, to maintain and support the distal portion of the tube holder, as well as a distal or forward portion of the tube holder, the fitting, and any tubing attached thereto. A third contoured portion 27c also depends from bottom wall 50c at a position opposite from the second contoured portion 17c. In the embodiment of FIGS. 24-25, third contoured portion 27c defines a first bump 127 and a second bump 128, with a valley 129 extending between the first and second bumps 127, 128. Further, a protuberance 130 extends from the bottom portion of second contoured portion 17c at the end of the longitudinal recess 25c. The first and second bumps 127, 128 and the valley 129 are sized and dimensioned such that, when two separate trays 12c are arranged in a nested relationship, the valley 129 of one tray accommodates the protuberance 130 of another tray. In this manner, two separate trays 12c can be appropriately nested together for packaging and transport. Also, protuberance 130 of one tray may fit within valley 129 of another tray in an interfering manner, thereby preventing any rotative movement of one tray with respect to another when nested, and thereby facilitating removal of two nested trays from a packaging container. Such an interference fit may include an attachment between the protuberance 130 of one tray and the valley 129 of another tray, such as in a snap fit manner.

It is further contemplated that portions of the tray body 13c may be undercut at inward-extending lips 65c in a similar manner as described above, so as to grip a section of the tubing in order to maintain the tubing within the internal space defined by tray body 13c prior to use of the device.

While the present invention is described with reference to several distinct embodiments of a prepackaged medical device and method, those skilled in the art may make modifications and alterations without departing from the scope and spirit. Accordingly, the above detailed description is intended to be illustrative rather than restrictive.

The invention claimed is:

1. A prepackaged medical device comprising:
a medical device comprising a needle assembly, a tube holder, and a length of tubing extending between the needle assembly and the tube holder; and
a tray supporting the medical device, said tray comprising:
a tray body defining a first contoured portion supporting and maintaining positioning of the needle assembly and a second contoured portion supporting and maintaining positioning of the tube holder, the first and second contoured portions formed in spaced relation with respect to each other to allow sequential removal of the needle assembly, tubing, and tube holder, wherein the second contoured portion has a depth that is different than a depth of the first contoured portion and wherein at least a portion of the second contoured portion depends from and extends below a bottom wall of the tray body, said at least a portion of the second contoured portion extending along a plane which is generally parallel to a plane formed by the bottom wall of the tray body wherein at least a portion of the bottom wall supports a portion of the tubing, and wherein the tray body comprises the bottom wall and a plurality of posts upstanding from the bottom wall in the first contoured portion, the posts positioned to maintain the needle assembly in a defined orientation until removal of the needle assembly; and
a removable lid enclosing the medical device.

2. The prepackaged medical device of claim 1 wherein the tray body defines a peripheral flange upon which the lid is engaged, the flange comprising at least one lip for maintaining the position of the tubing within the tray body prior to removal of the needle assembly.

3. The prepackaged medical device of claim 1 wherein at least a portion of the second contoured portion is formed to accept the tube holder.

4. The prepackaged medical device of claim 1 wherein the first contoured portion of the tray body is adapted to maintain the needle assembly within the tray body in at least two distinct orientations with respect to the orientation of the tube holder maintained within the tray body.

5. The prepackaged medical device of claim 4 wherein one of the orientations is for accommodating tubing having a first length and another of the orientations is for accommodating tubing having a second length longer or shorter than the first length by at least about 20 percent.

6. The prepackaged medical device of claim 1 wherein the plurality of posts are arranged to maintain the needle assembly within the tray body in at least two distinct orientations with respect to the orientation of the tube holder maintained within the tray body.

7. The prepackaged medical device of claim 1 wherein the needle assembly comprises a pair of outward-extending wings, the plurality of posts positioned to maintain a defined orientation of the wings until removal of the needle assembly.

8. The prepackaged medical device of claim 7 wherein the plurality of posts are arranged to allow the wings to be oriented in two generally oppositely facing orientations.

9. The prepackaged medical device of claim 1 wherein the tray body comprises the bottom wall and at least one post upstanding from the bottom wall and adapted to maintain the positioning of the tubing relative to the needle assembly.

10. The prepackaged medical device of claim 9 wherein the needle assembly comprises a distally-extending needle cannula, and the at least one post is positioned to maintain the positioning of the tubing relative to the needle cannula to prevent the needle cannula from damaging the tubing during shipment of the prepackaged medical device.

11. The prepackaged medical device of claim 10 wherein the relative positioning between the tubing and the needle cannula comprises the needle cannula restraining the tubing against the bottom wall of the tray body.

12. The prepackaged medical device of claim 9 wherein the needle assembly comprises a distally-extending needle cannula and a safety cap enclosing the needle cannula, and the at least one post is positioned to maintain the positioning of the tubing relative to the safety cap and the shield to prevent the tubing from interfering with the safety cap and the shield during removal of the needle assembly.

13. The prepackaged medical device of claim 12 wherein the relative positioning between the tubing and safety cap comprises the safety cap restraining the tubing against the bottom wall of the tray body.

14. The prepackaged medical device of claim 1 wherein at least a portion of the second contoured portion depends from a bottom wall of the tray body, and the tray body further comprises a third contoured portion depending from the bottom wall of the tray body at a position opposite to and spaced from the second contoured portion with respect to the bottom wall of the tray body, the second and third contoured portions formed to allow the tray body to nest with another tray body.

15. The prepackaged medical device of claim 1 wherein the second contoured portion includes a recess having a depth with respect to the tray body which is greater than a depth with respect to the tray body of the first contoured portion.

16. The prepackaged medical device of claim 1 wherein the tray body is configured such that at least a portion of the tubing is positioned adjacent a top surface of a bottom wall of the tray body.

17. The prepackaged medical device of claim 1 wherein at least a portion of the second contoured portion extends below a plane extending through the first contoured portion.

18. A medical kit comprising:
a needle assembly;
a fitting;
a tube holder attached to the fitting;
a length of tubing connecting the needle assembly and the fitting; and
a tray comprising:
a tray body defining a first contoured portion supporting and maintaining positioning of the needle assembly and a second contoured portion supporting and maintaining positioning of the tube holder and fitting, the first and second contoured portions formed in spaced relation with respect to each other to allow first removal of the needle assembly, second removal of the tubing, and third removal of the fitting and the attached tube holder, wherein the second contoured portion has a depth that is different than a depth of the first contoured portion and wherein the second contoured portion depends from and extends below a bottom wall of the tray body, at least a portion of said second contoured portion extending along a plane which is generally parallel to a plane formed by the bottom wall of the tray body wherein at least a portion of the bottom wall supports a portion of the tubing, and wherein the tray body comprises the bottom wall and a plurality of posts upstanding from the bottom wall in the first contoured portion, the posts positioned to maintain the needle assembly in a defined orientation until removal of the needle assembly; and
a removable lid enclosing the medical kit.

19. A prepackaged medical device comprising:
a medical device comprising a needle assembly, a tube holder, and a length of tubing extending between the needle assembly and the tube holder; and
a tray supporting the medical device, said tray comprising:
a tray body defining a first contoured portion supporting and maintaining positioning of the needle assembly and a second contoured portion spaced from the first contoured portion, said second contoured portion configured for supporting and maintaining positioning of the tube holder, the first contoured portion comprising structure adapted to maintain the needle assembly within the tray body in at least two distinct orientations with respect to the orientation of the tube holder maintained within the tray body, wherein the second contoured portion has a depth that is different than a depth of the first contoured portion and wherein the second contoured portion depends from and extends below a bottom wall of the tray body, at least a portion of said second contoured portion extending along a plane which is generally parallel to a plane formed by the bottom wall of the tray body wherein at least a portion of the bottom wall supports a portion of the tubing, and wherein the tray body comprises the bottom wall and a plurality of posts upstanding from the bottom wall in the first contoured portion, the posts positioned to maintain the needle assembly in a defined orientation until removal of the needle assembly; and
a removable lid enclosing the medical device.

20. The prepackaged medical device of claim 19, wherein the structure of the first contoured portion maintains the needle assembly within the tray body in a first orientation for accommodating tubing having a first length and in a second orientation for accommodating tubing having a second length longer or shorter than the first length by at least about 20 percent.

21. A prepackaged medical device comprising:
a medical device comprising a needle assembly, a tube holder, and a length of tubing extending between the needle assembly and the tube holder; and
a tray supporting the medical device, said tray comprising a tray body defining a first contoured portion supporting and maintaining positioning of the needle assembly, a second contoured portion spaced from the first portion and depending from a bottom wall of the tray body for supporting and maintaining positioning of the tube holder, and a third contoured portion depending from the bottom wall of the tray body at a position opposite from the second contoured portion, the second and third contoured portions formed to allow the tray body to nest with another tray body and the second contoured portion having a depth that is different than a depth of the first contoured portion and wherein the second contoured portion depends from and extends below a bottom wall of the tray body, at least a portion of said second contoured portion extending along a plane which is generally parallel to a plane formed by the bottom wall of the tray body wherein at least a portion of the bottom wall supports a portion of the tubing, and wherein the tray body comprises the bottom wall and a plurality of posts upstanding from the bottom wall in the first contoured portion, the posts positioned to maintain the needle assembly in a defined orientation until removal of the needle assembly.

22. The prepackaged medical device of claim 21, wherein the second and third contoured portions extend from the bottom wall of the tray body such that a plane extending across bottom portions of the second and third contoured portions is generally parallel with the bottom wall of the tray body.

* * * * *